US010150949B2

(12) United States Patent
Yamanaka et al.

(10) Patent No.: US 10,150,949 B2
(45) Date of Patent: Dec. 11, 2018

(54) CARDIOMYOCYTE MARKER

(71) Applicant: KYOTO UNIVERSITY, Kyoto (JP)

(72) Inventors: Shinya Yamanaka, Kyoto (JP);
Yoshinori Yoshida, Kyoto (JP);
Shunsuke Funakoshi, Kyoto (JP)

(73) Assignee: Kyoto University, Kyoto (JP)

( * ) Notice: Subject to any disclaimer, the term of this patent is extended or adjusted under 35 U.S.C. 154(b) by 0 days.

(21) Appl. No.: 15/619,842

(22) Filed: Jun. 12, 2017

(65) Prior Publication Data

US 2017/0335285 A1 Nov. 23, 2017

Related U.S. Application Data

(62) Division of application No. 14/414,210, filed as application No. PCT/JP2013/069721 on Jul. 16, 2013.

(Continued)

(51) Int. Cl.
*G01N 33/566* (2006.01)
*G01N 33/74* (2006.01)
(Continued)

(52) U.S. Cl.
CPC ....... *C12N 5/0657* (2013.01); *G01N 33/5005* (2013.01); *G01N 33/566* (2013.01); *G01N 33/56966* (2013.01); *G01N 33/74* (2013.01); *G01N 33/92* (2013.01); *C12N 2500/02* (2013.01); *C12N 2501/115* (2013.01); *C12N 2501/155* (2013.01); *C12N 2501/165* (2013.01);
(Continued)

(58) Field of Classification Search
CPC .............. C12N 5/0657; C12N 2500/02; C12N 2501/20; C12N 2501/115; C12N 2501/155; C12N 2501/165; C12N 2501/415; C12N 2506/45; G01N 33/5005; G01N 33/566; G01N 33/56966; G01N 33/74; G01N 33/92; G01N 2405/10; G01N 2333/91205
See application file for complete search history.

(56) References Cited

U.S. PATENT DOCUMENTS 7,897,389 B2 * 3/2011 Gold .................... C12N 5/0657
435/363
9,164,093 B2 10/2015 Yamashita et al.
(Continued)

FOREIGN PATENT DOCUMENTS

JP 2004-535199 A 11/2004
JP 2007-528755 A 10/2007
(Continued)

OTHER PUBLICATIONS

Zhao et al. Neuregulins Promote Survival and Growth of Cardiac Myocytes. The Journal of Biological Chemistry. 278 (17): 10261-10269 (Apr. 1998).*

(Continued)

*Primary Examiner* — Gailene Gabel
(74) *Attorney, Agent, or Firm* — Knobbe, Martens Olson & Bear, LLP

(57) ABSTRACT

The present invention provides a method for producing or detecting cardiomyocytes by extracting/detecting cardiomyocytes from a cell population which includes cardiomyocytes using, as an index, positivity of NCAM1, SSEA3, SSEA4 and/or CD340.

17 Claims, 42 Drawing Sheets

Related U.S. Application Data

(60) Provisional application No. 61/672,637, filed on Jul. 17, 2012.

(51) Int. Cl.
*G01N 33/92* (2006.01)
*C12N 5/077* (2010.01)
*G01N 33/50* (2006.01)
*G01N 33/569* (2006.01)

(52) U.S. Cl.
CPC .... *C12N 2501/20* (2013.01); *C12N 2501/415* (2013.01); *C12N 2506/45* (2013.01); *G01N 2333/91205* (2013.01); *G01N 2405/10* (2013.01)

(56) References Cited

U.S. PATENT DOCUMENTS

| | | |
|---|---|---|
| 2003/0022367 A1 | 1/2003 | Xu |
| 2007/0010012 A1 | 1/2007 | Gold et al. |
| 2007/0092492 A1 | 4/2007 | Matsuda et al. |
| 2009/0068742 A1 | 3/2009 | Yamanaka |
| 2010/0009399 A1 | 1/2010 | Sartipy et al. |
| 2011/0033430 A1 | 2/2011 | Chien et al. |
| 2011/0104122 A1 | 5/2011 | Yamashita et al. |
| 2011/0117575 A1* | 5/2011 | Buehring ............ C07K 16/2803 435/7.21 |
| 2011/0212480 A1* | 9/2011 | Kolaja ................ G01N 33/5061 435/29 |
| 2013/0230921 A1 | 9/2013 | Keller et al. |
| 2014/0057287 A1 | 2/2014 | Yamashita et al. |

FOREIGN PATENT DOCUMENTS

| | | |
|---|---|---|
| JP | 2009-542237 A | 12/2009 |
| JP | 2010-517578 A | 5/2010 |
| JP | 2010-158206 A | 7/2010 |
| WO | WO 2005/090558 A1 | 9/2005 |
| WO | WO 2007/002136 A2 | 1/2007 |
| WO | WO 2007/069666 A1 | 6/2007 |
| WO | WO 2009/118928 A | 10/2009 |
| WO | WO 2012/024782 A1 | 3/2012 |
| WO | WO 2012/133954 A1 | 10/2012 |
| WO | WO 2012/162741 A1 | 12/2012 |

OTHER PUBLICATIONS

International Search Report for International Application No. PCT/JP2013/069721, dated Oct. 22, 2013.

Written Opinion of the International Searching Authority for International Application No. PCT/JP2013/069721, dated Oct. 22, 2013.

Dubois et al., "SIRPA is a specific cell-surface marker for isolating cardiomyocytes derived from human pluripotent stem cells," Nature Biotechnology, vol. 29(11), pp. 1011-1018 (Nov. 2011).

Honda et al., "N-cadherin is a useful marker for the progenitor of cardiomyocytes differentiated from mouse ES cells in serum-free condition," Biochem Biophys Res Commun., vol. 351, pp. 877-882 (2006).

Rust et al., "Cardiomyocyte enrichment from human embryonic stem cell cultures by selection of ALCAM surface expression," Regen Med., vol. 4(2), pp. 225-237 (Mar. 2009) (abstract only).

Uosaki et al., "Efficient and Scalable Purification of Cardiomyocytes from Human Embryonic and Induced Pluripotent Stem Cells by VCAM1 Surface Expression," PLOS One, vol. 6(8), p. e23657 (Aug. 2011).

Yan et al., "Cyclosporin-A potently induces highly cardiogenic progenitors from embryonic stem cells," Biochem Biophys Res Commun., vol. 379, pp. 115-120 (2009).

Office Action issued in corresponding Japanese Patent Application No. 2015-503601, dated May 23, 2017.

Zhao et al., "Neuregulins Promote Survival and Growth of Cardiac Myocytes," *The Journal of Biological Chemistry*, vol. 273(17), pp. 10261-10269 (Apr. 24, 1998).

\* cited by examiner

Day4

Day12

Day26

Day60

Negative

NCAM-brilliant violet

NCAM low

NCAM high

Day4

Day8

Day16

Day26

Day33

Day45

Day60

Day8

Day12

Day26

Day33

Day45

Day60

Day4

Day8

Day16

Day30

Day45

CARDIOMYOCYTE MARKER

CROSS-REFERENCE TO RELATED APPLICATIONS

This application is a divisional of U.S. application Ser. No. 14/414,210, filed Jan. 12, 2015 which is the U.S. National Phase under 35 U.S.C. § 371 of International Application PCT/JP2013/069721, filed Jul. 16, 2013, which claims priority to U.S. 61/672,637, filed Jul. 17, 2012.

FIELD OF INVENTION

The present invention relates to novel cardiomyocyte markers for extracting/detecting cardiomyocytes from a cell population comprising the cardiomyocytes.

BACKGROUND ART

Since cardiomyocytes lose their division potential at the time of birth and hence their regeneration is difficult, recent interest has focused on replacement therapy wherein cardiomyocytes obtained by inducing differentiation of cells having pluripotency (WO/2007/069666), such as embryonic stem cells (ES cells) or induced pluripotent stem cells (iPS cells), are transplanted to a cardiac tissue damaged due to myocardial infarction, myocarditis, aging or the like. Although many methods for inducing differentiation of such pluripotent stem cells into cardiomyocytes have been reported (WO2007/002136, WO2009/118928 and Yan P, et al., Biochem Biophys Res Commun. 379:115-20 (2009)), use of the induced cells in transplantation further requires enhancement of the purity of the cardiomyocytes by sorting or the like. Although, at present, CD166 (ALCM) (Rust W, et al., Regen Med. 4, 225-37 (2009)), N-cadherin (JP 2010-158206 A and Honda M, et al., Biochem Biophys Res Commun. 29, 351, 877-82 (2006)), VCAM1 (International Application No. PCT/JP2012/059617) and the like have been reported as surface markers for cardiomyocytes, it is thought that more markers are necessary for enhancement of the purity of cardiomyocytes.

SUMMARY OF THE INVENTION

An object of the present invention is to extract/detect cardiomyocytes from a cell population comprising the cardiomyocytes. Accordingly, the present invention aims to provide markers specific for cardiomyocytes.

In order to solve the above problem, the inventors of the present invention focused on NCAM1, SSEA3, SSEA4 and CD340, and discovered that, by using positivity of at least one of these as an index, cardiomyocytes can be obtained at high efficiency from a cell population containing cardiomyocytes obtained by inducing differentiation of pluripotent stem cells.

Based on the above knowledge, the inventors of the present invention succeeded in isolation and purification of cardiomyocytes by using, as an index, positivity of at least one selected from the group consisting of NCAM1, SSEA3, SSEA4 and CD340, thereby completed the present invention.

It is one aspect of the present invention to provide a method for producing a cardiomyocyte(s), comprising
a) providing a cell population comprising the cardiomyocyte(s), and
b) extracting a cardiomyocyte(s) from the cell population comprising the cardiomyocyte(s) using, as an index, positivity of at least one selected from the group consisting of NCAM1, SSEA3, SSEA4 and CD340.

It is another aspect of the present invention to provide the method as described above, wherein said cardiomyocyte is human cardiomyocyte.

It is another aspect of the present invention to provide the method as described above, wherein said cell population comprising cardiomyocyte(s) is a cell population obtained by inducing differentiation of a pluripotent stem cell(s), or a cell population composed of cells of an isolated tissue(s).

It is another aspect of the present invention to provide the method as described above, wherein said pluripotent stem cell is an ES cell or iPS cell.

It is another aspect of the present invention to provide the method as described above, wherein said induction of differentiation into a cardiomyocyte(s) comprises forming an embryoid body.

It is another aspect of the present invention to provide the method as described above, wherein said induction of differentiation into a cardiomyocyte(s) comprises culturing an embryoid body in a medium comprising a cytokine(s).

It is another aspect of the present invention to provide the method as described above, wherein said cytokine(s) is at least one cytokine selected from the group consisting of activin A, BMP4, b-FGF, and VEGF.

It is another aspect of the present invention to provide the method as described above, wherein said medium further comprises a Wnt inhibitor.

It is another aspect of the present invention to provide the method as described above, wherein said Wnt inhibitor is DKK-1.

It is another aspect of the present invention to provide a method for detecting a cardiomyocyte(s), comprising detecting a cardiomyocyte(s) in a cell population comprising a cardiomyocyte using, as an index, positivity of at least one selected from the group consisting of NCAM1, SSEA3, SSEA4 and CD340.

It is another aspect of the present invention to provide the method as described above, wherein said cardiomyocyte is human cardiomyocyte.

It is another aspect of the present invention to provide the method as described above, wherein said cell population comprising a cardiomyocyte is a cell population obtained by inducing differentiation of a pluripotent stem cell(s), or a cell population composed of cells of an isolated tissue(s).

It is another aspect of the present invention to provide the method as described above, wherein said pluripotent stem cell is an ES cell or iPS cell.

It is another aspect of the present invention to provide a kit for extracting or detecting a cardiomyocyte(s), comprising a reagent for detecting at least one selected from the group consisting of NCAM1, SSEA3, SSEA4 and CD340.

It is another aspect of the present invention to provide the kit as described above, wherein said cardiomyocyte is a human cardiomyocyte.

BRIEF DESCRIPTION OF THE DRAWINGS

In FIGS. 2A-2J, the ordinate indicates the intensity of NCAM1, and the abscissa indicates the intensity of EGFP.

In FIGS. 4A-4J, the ordinate indicates the intensity of SSEA3, and the abscissa indicates the intensity of EGFP.

In FIGS. 5A-5J, the ordinate indicates the intensity of SSEA4, and the abscissa indicates the intensity of EGFP.

In FIGS. 6A-6H, the ordinate indicates the intensity of CD340, and the abscissa indicates the intensity of EGFP.

EMBODIMENTS FOR CARRYING OUT THE INVENTION

Figure 1:
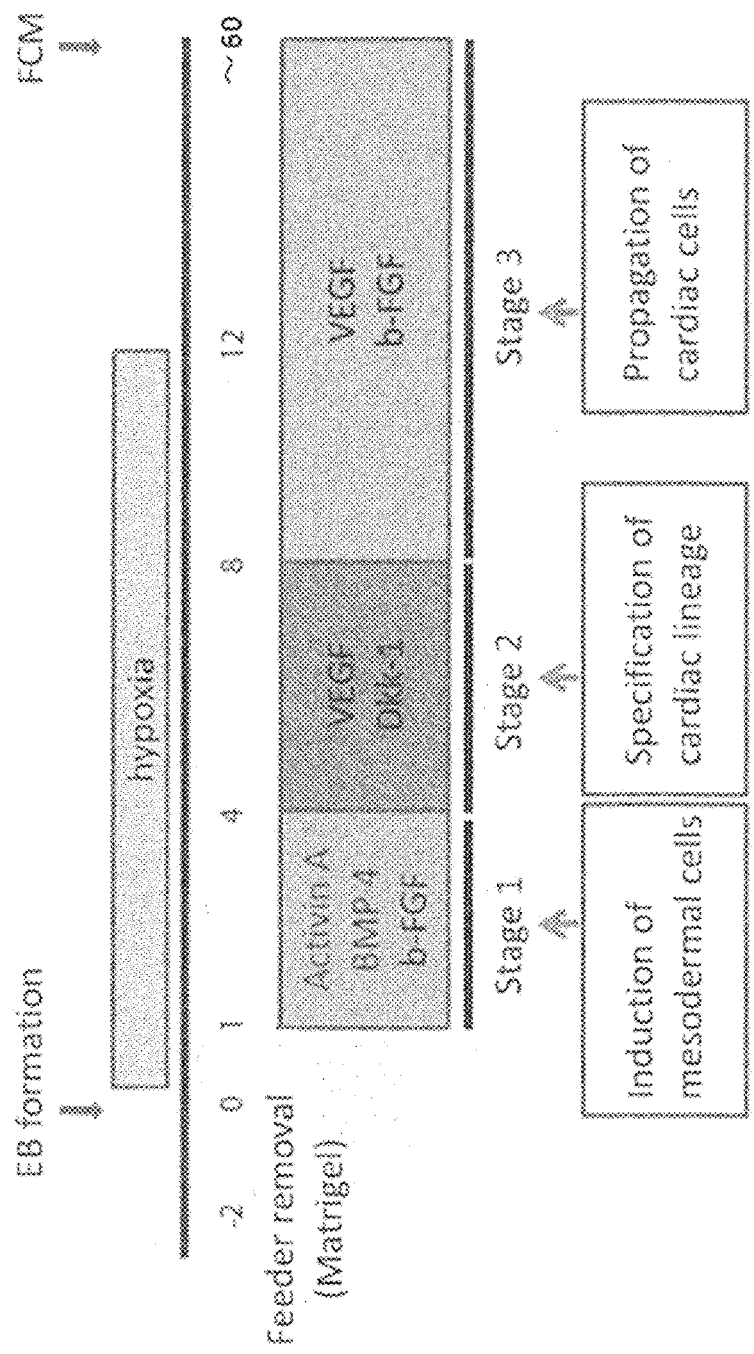
FIG. 1 is a protocol for inducing differentiation of pluripotent cells into cardiomyocytes.
Figure 2A:
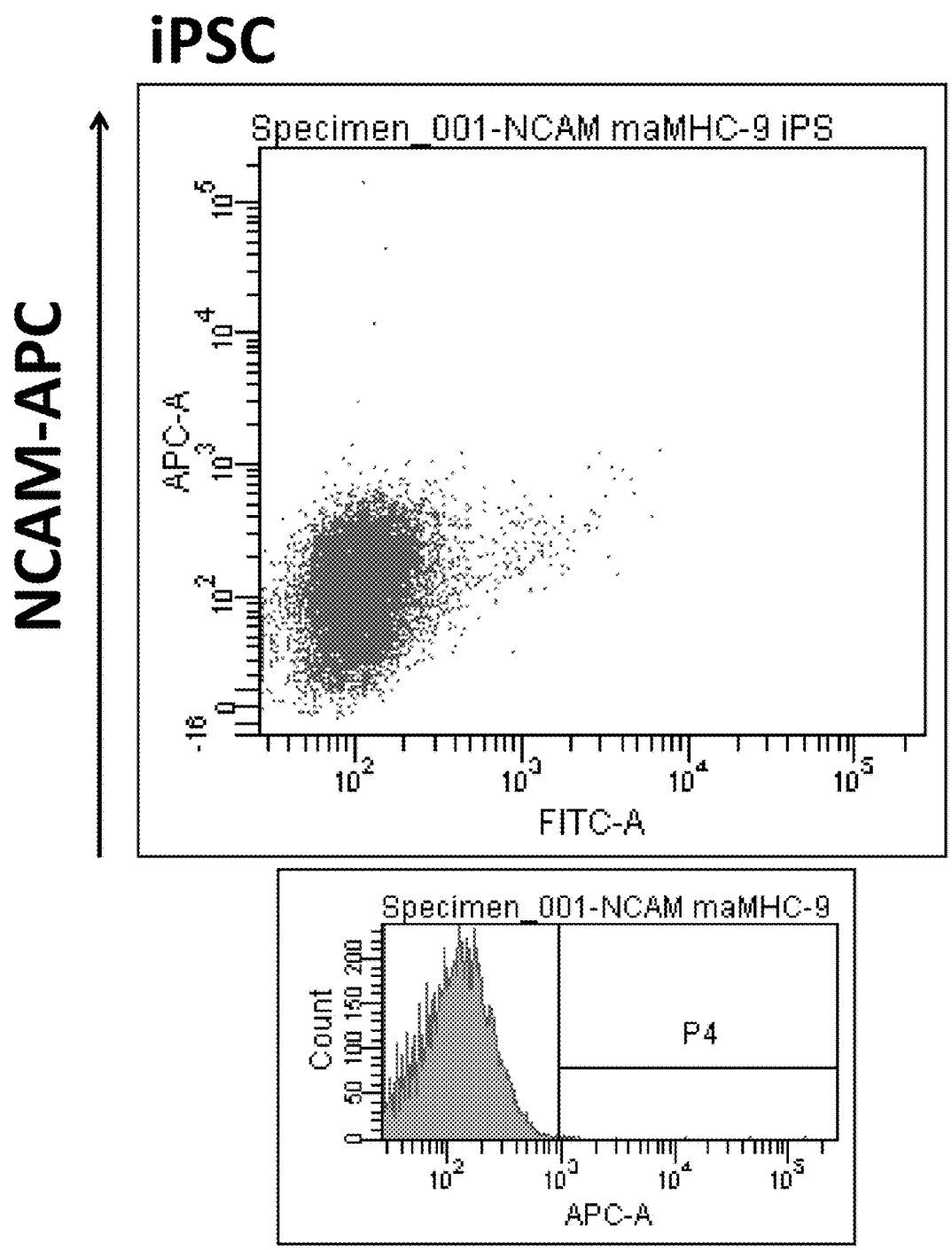
FIGS. 2A-2J illustrate the results of flow cytometry on Day 0 (FIG. 2A), Day 4 (FIG. 2B), Day 8 (FIG. 2C), Day 12 (FIG. 2D), Day 16 (FIG. 2E), Day 20 (FIG. 2F), Day 26 (FIG. 2G), Day 33 (FIG. 2H), Day 45 (FIG. 2I) and Day 60 (FIG. 2J) after the beginning of induction of differentiation of the 201B7-M6GIP4 strain.
Figure 2B:
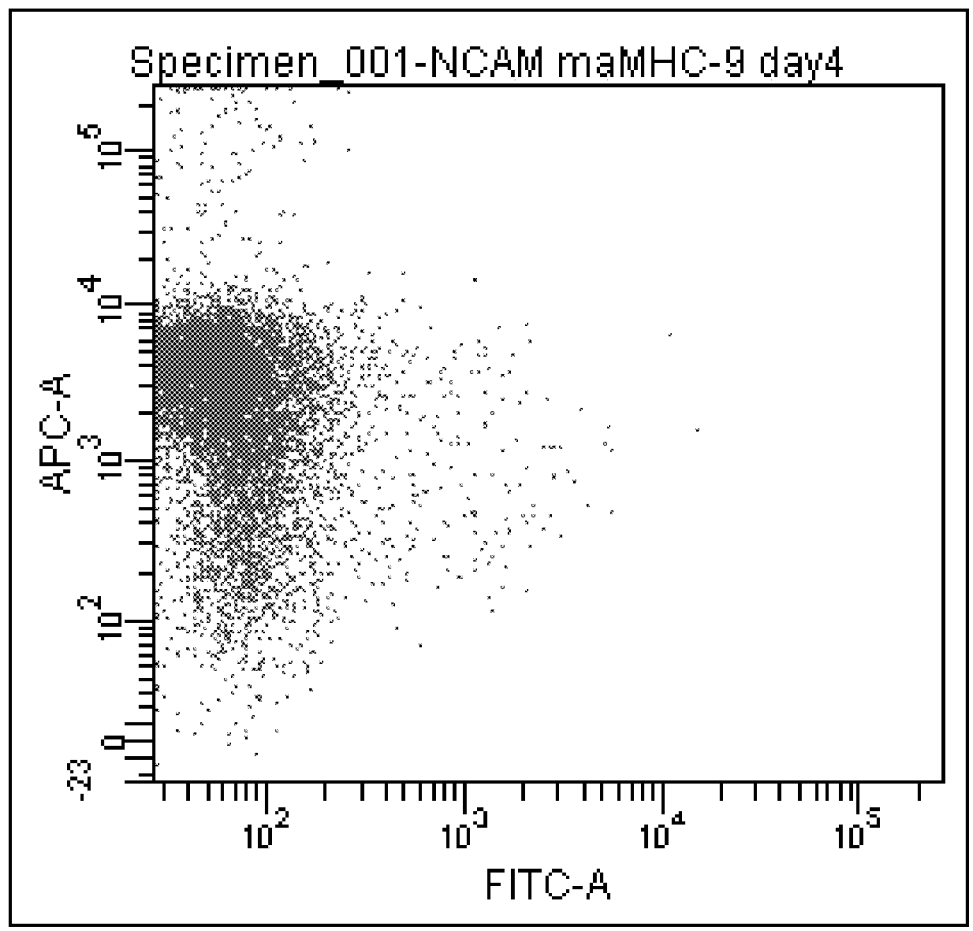
Figure 2B:
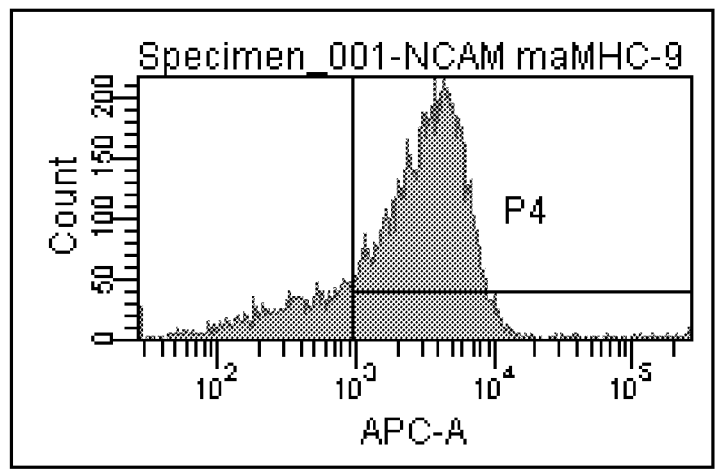
Figure 2C:
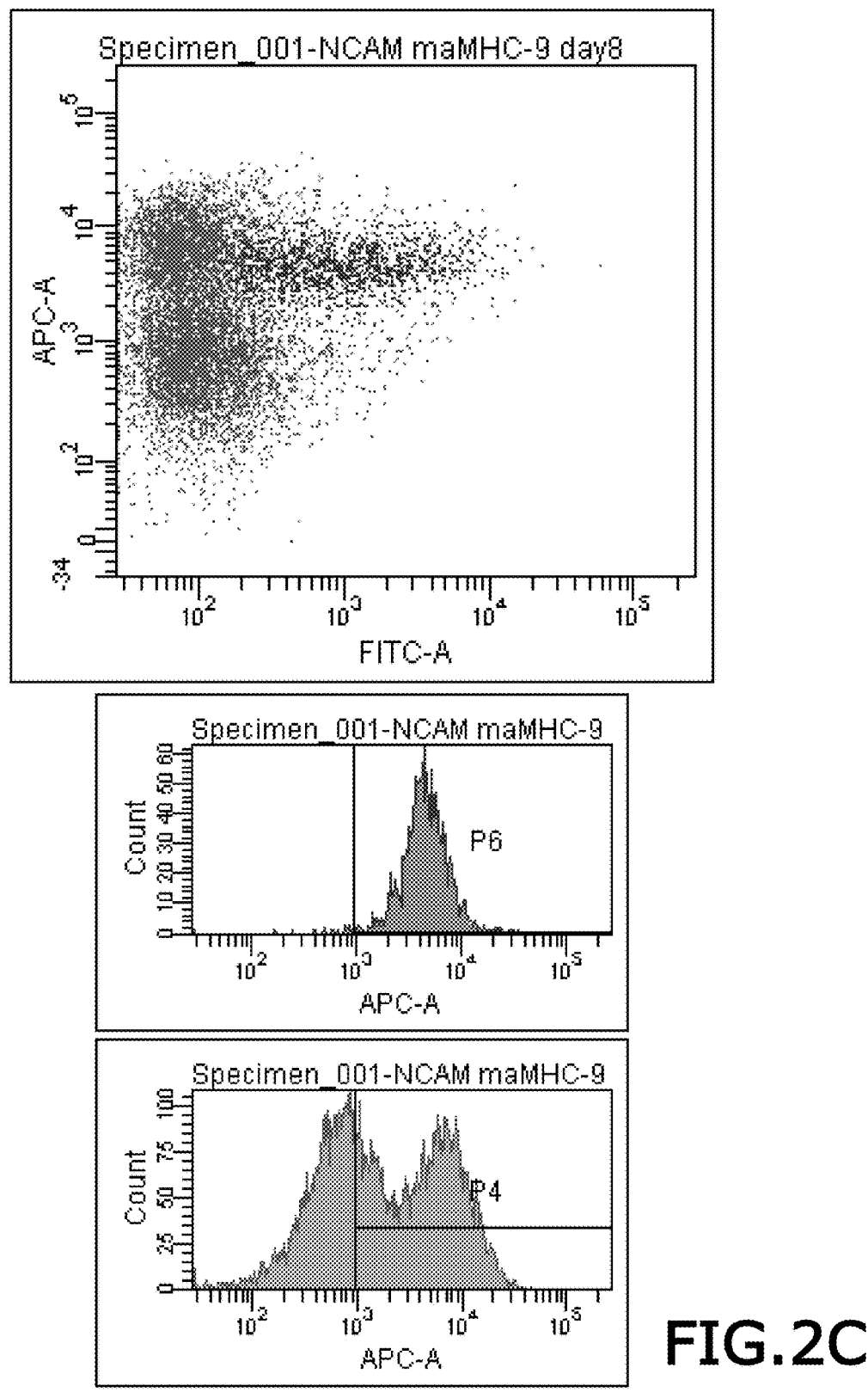
Figure 2D:
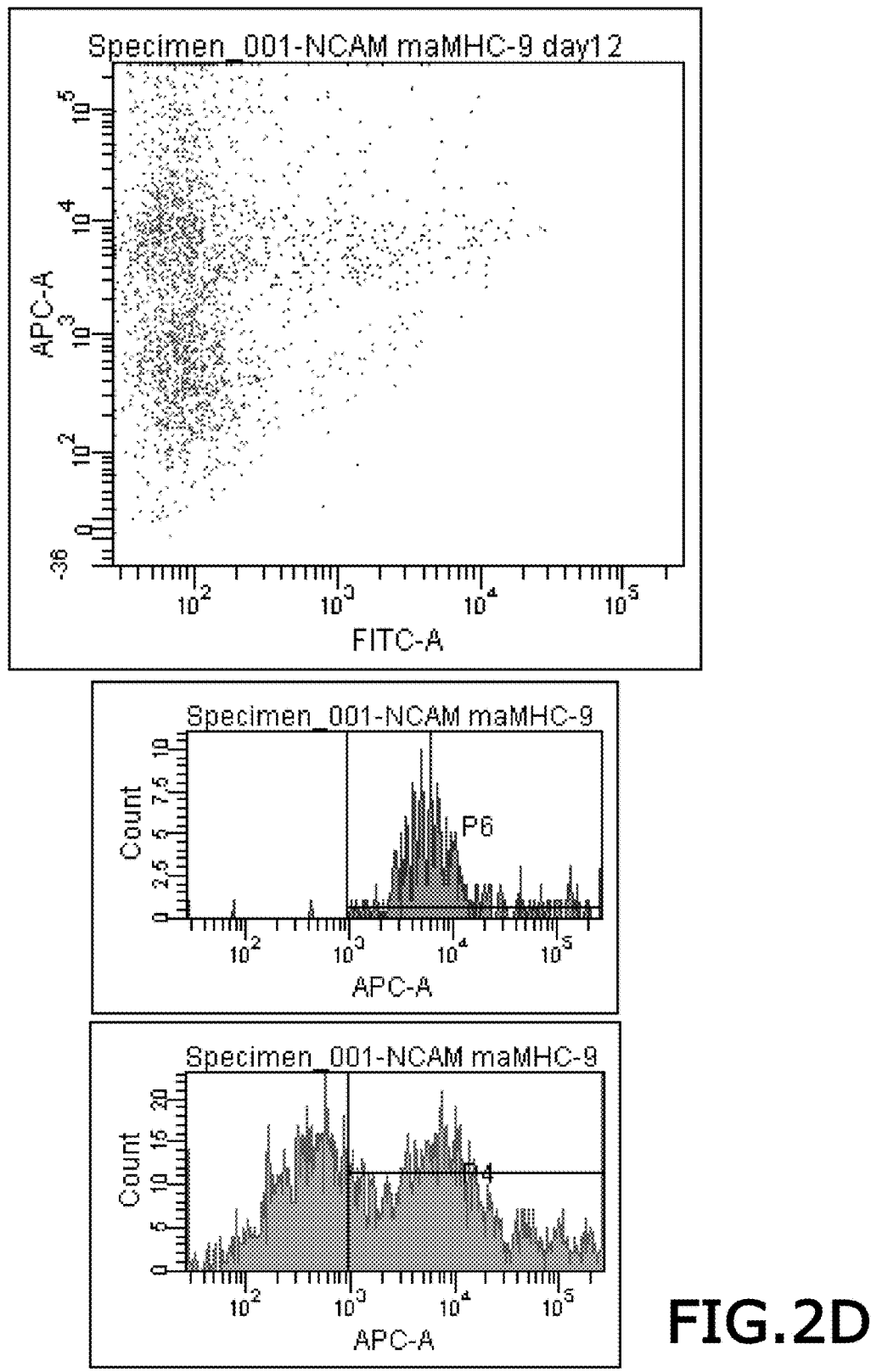
Figure 2E:
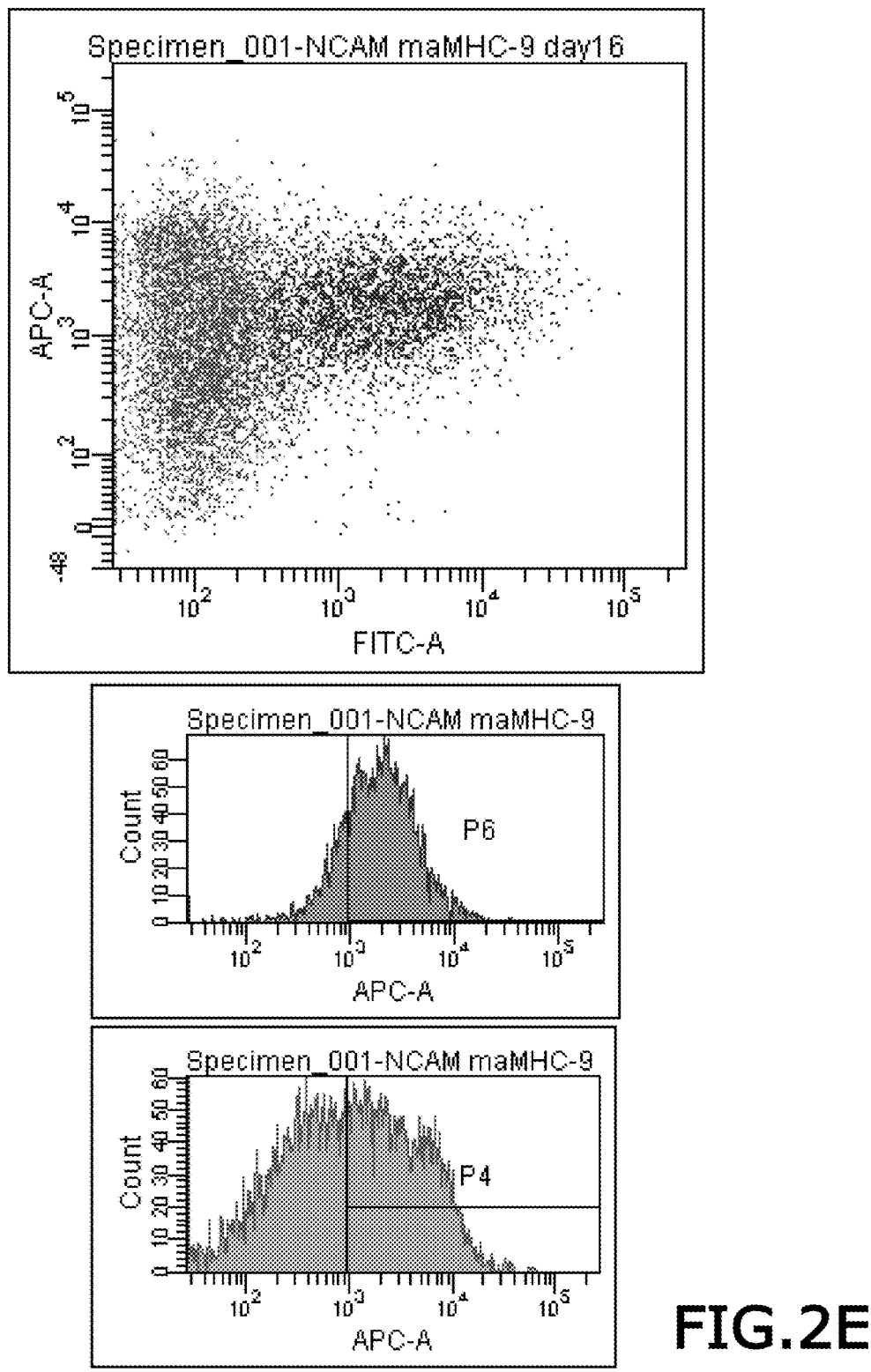
Figure 2F:
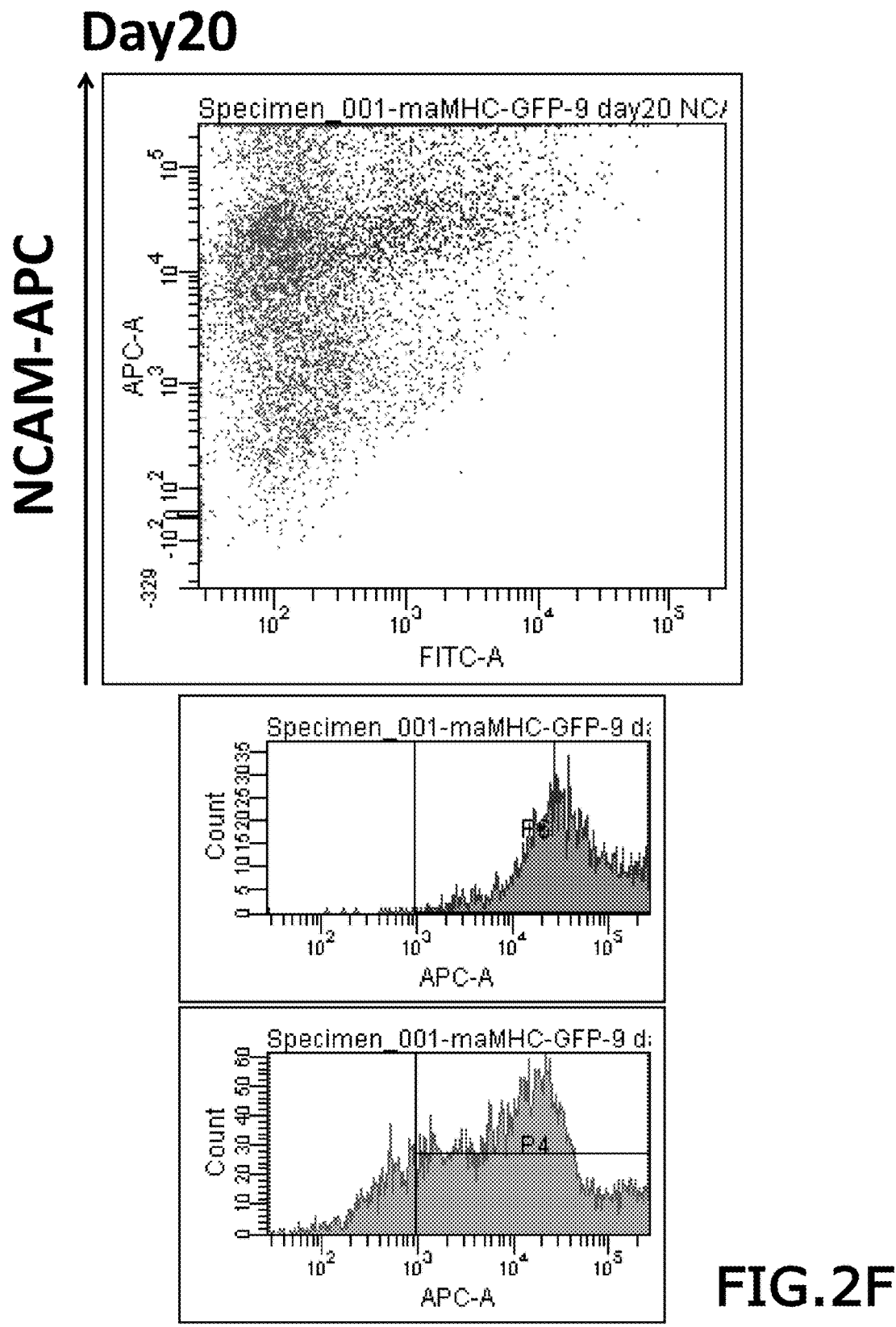
Figure 2G:
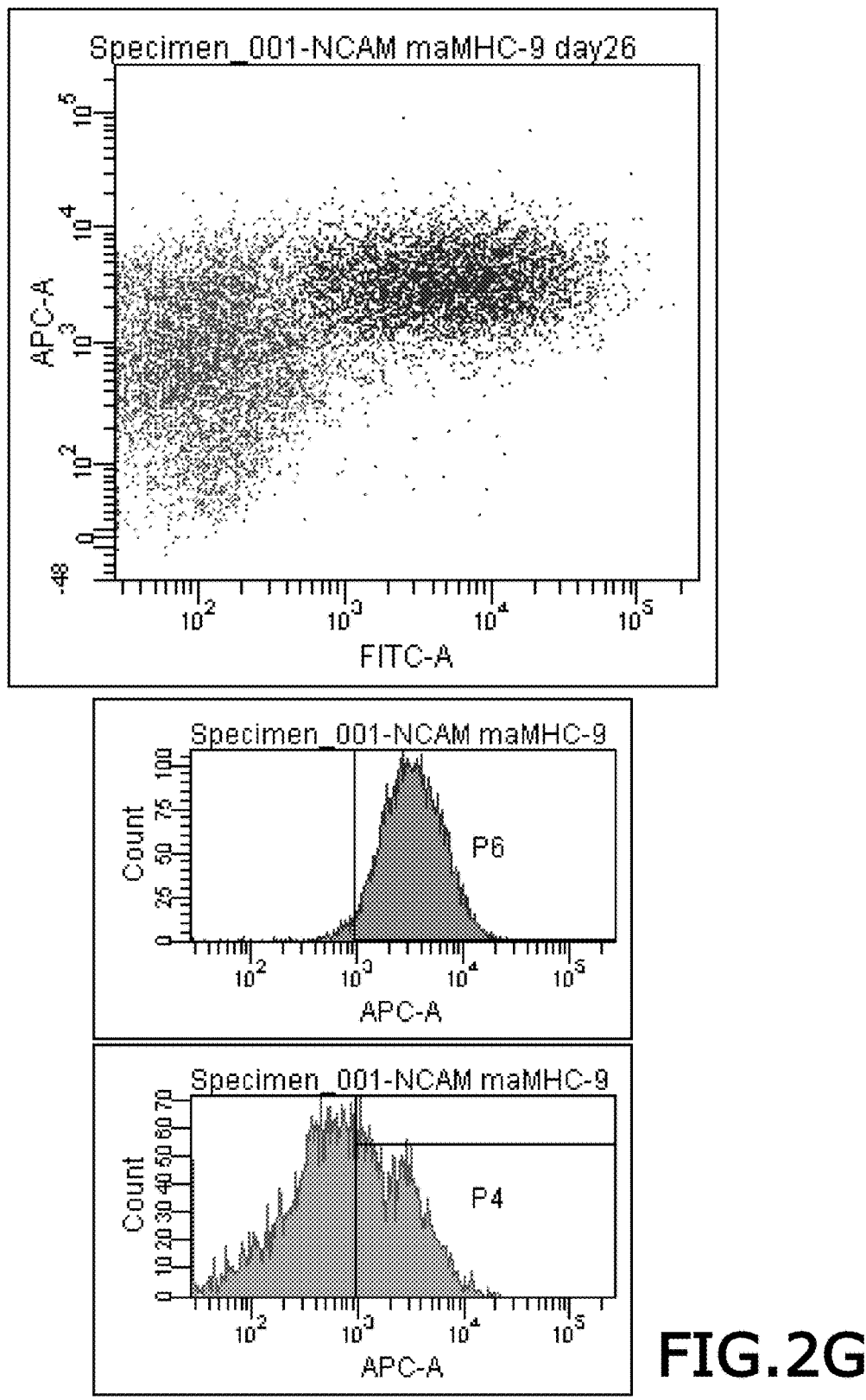
Figure 2H:
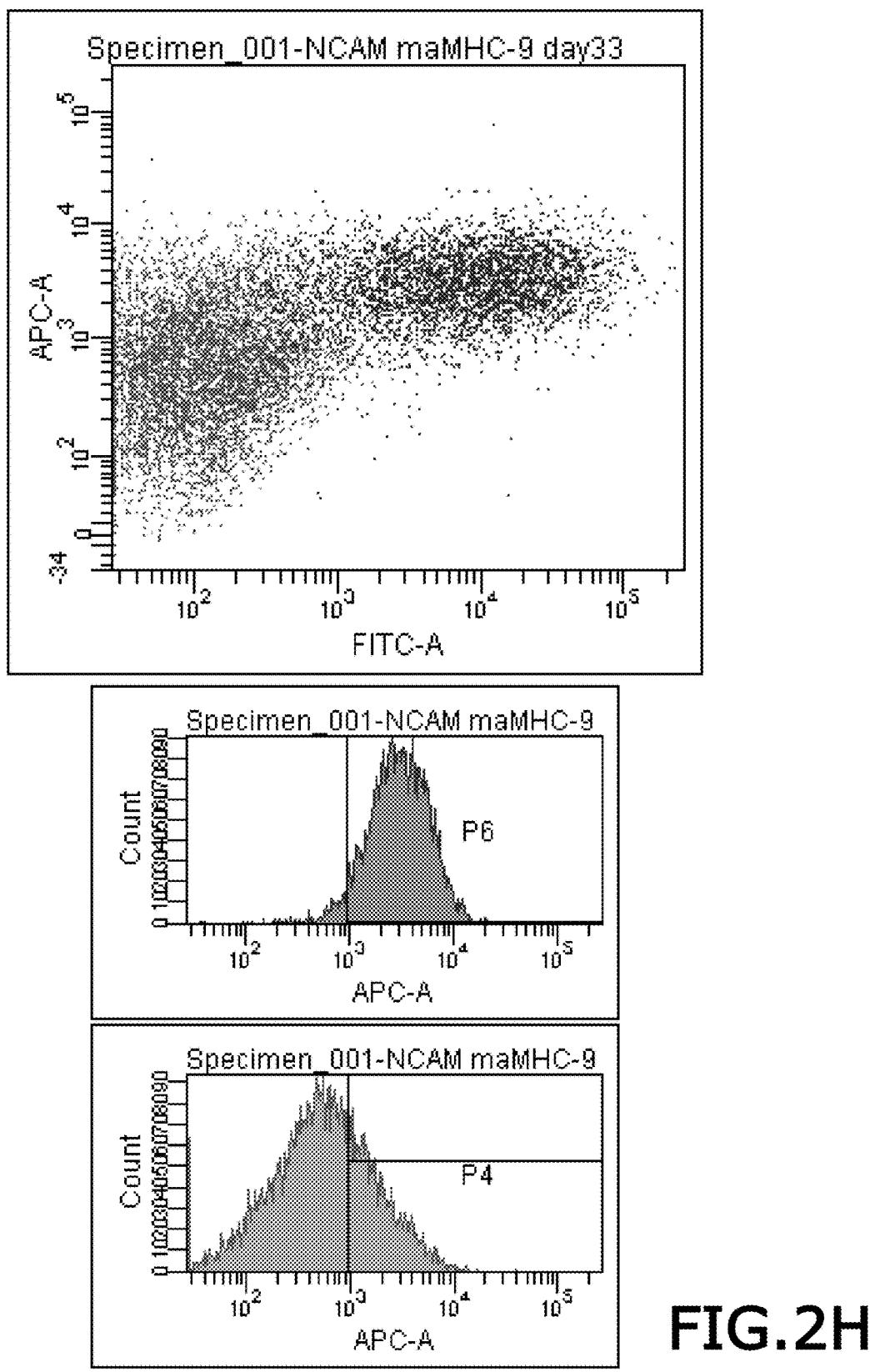
Figure 2I:
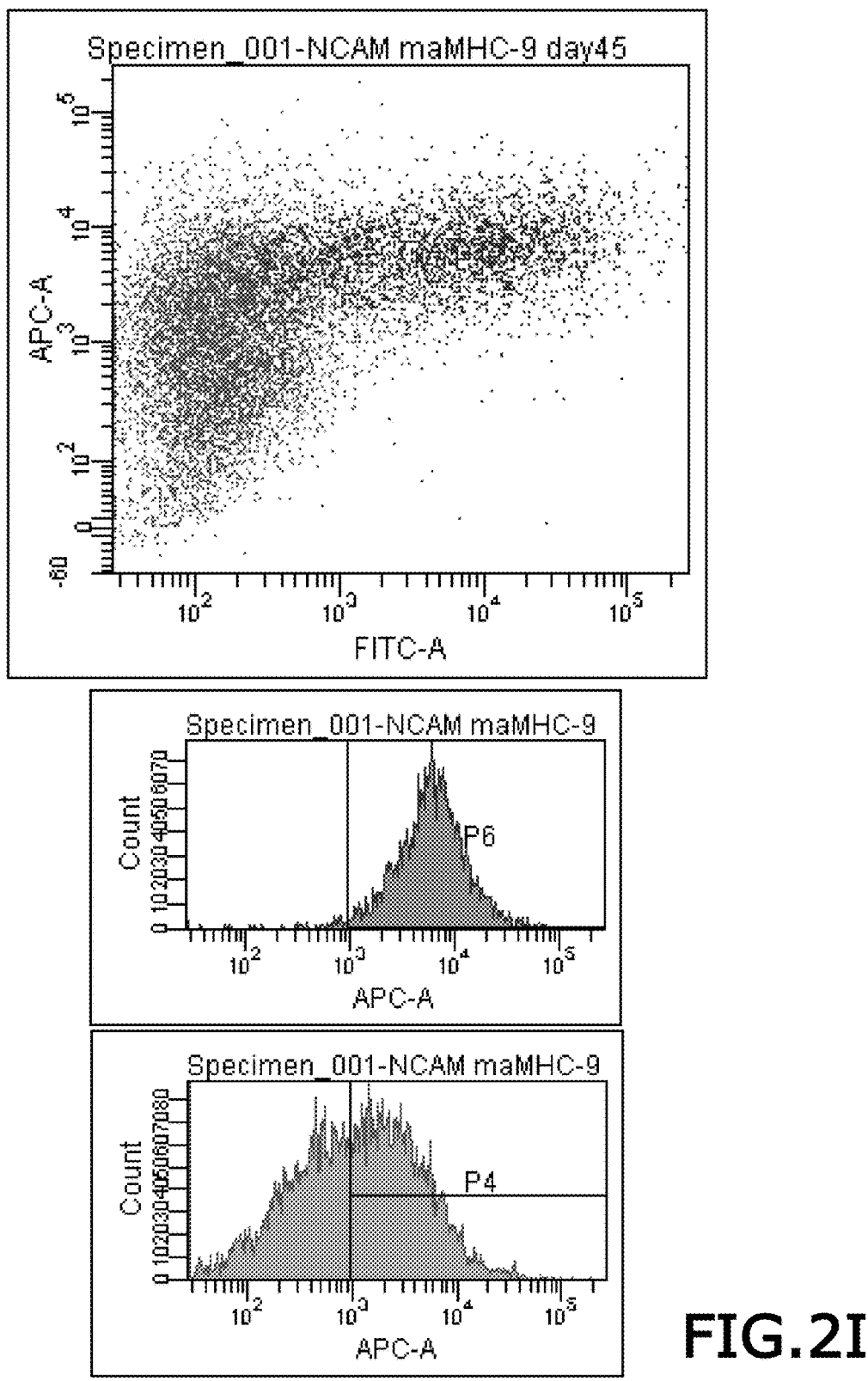
Figure 2J:
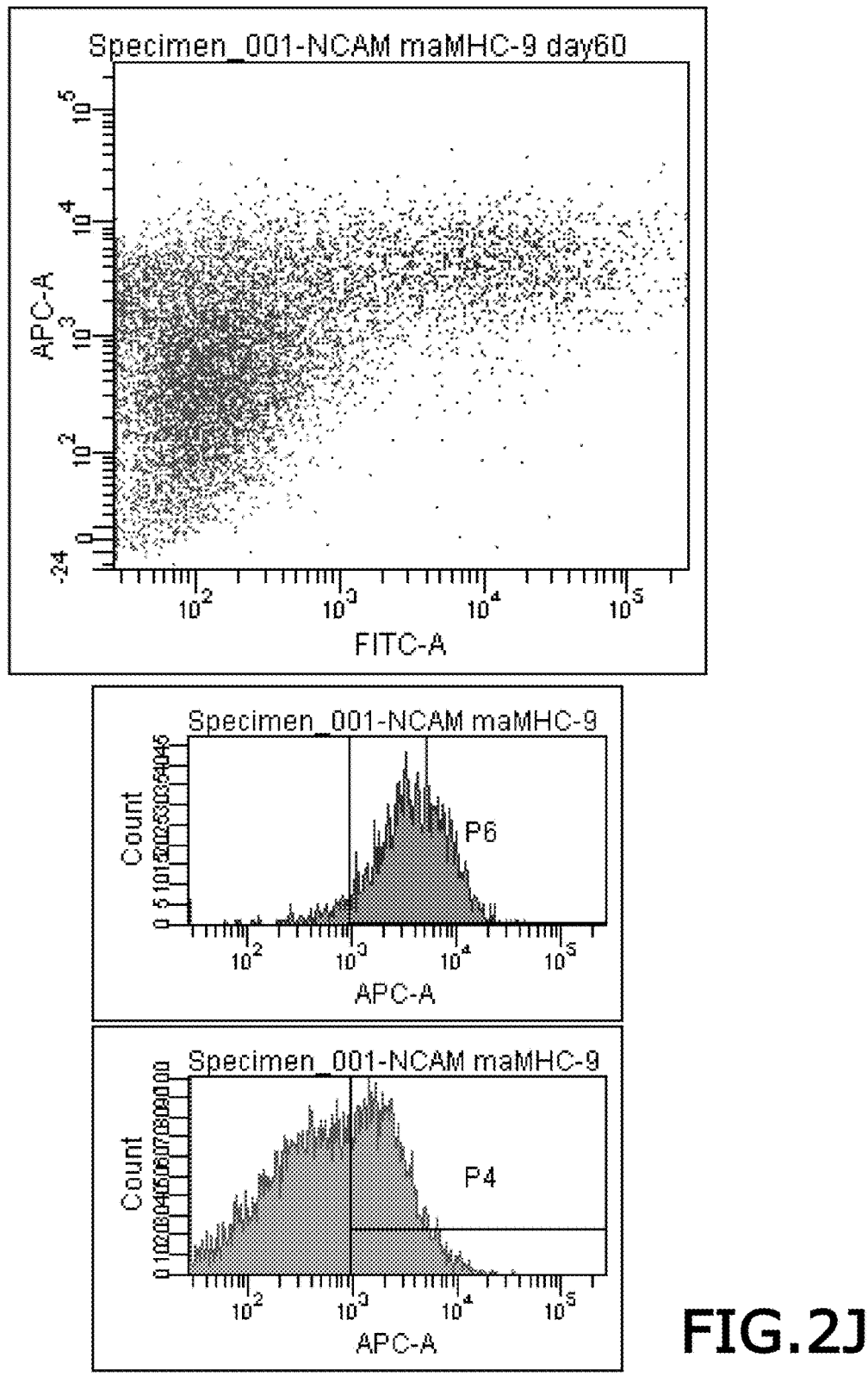

The present invention is described below in detail.

As described below, the present invention relates to a method for producing a cardiomyocyte(s), comprising extracting a cardiomyocyte(s) from a cell population comprising a cardiomyocyte using, as an index, positivity of at least one selected from the group consisting of NCAM1, SSEA3, SSEA4 and CD340, and a method for detecting a cardiomyocyte(s), comprising detecting a cardiomyocyte(s) in a cell population comprising a cardiomyocyte using, as an index, positivity of at least one selected from the group consisting of NCAM1, SSEA3, SSEA4 and CD340.

The origin of the cell population comprising a cardiomyocyte is not restricted as long as the cell population comprises a cardiomyocyte. Examples of the cell population include cells contained in peripheral blood, heart, myeloid tissue, adipose tissue, skeletal muscle tissue, amniotic tissue, placental tissue, umbilical cord blood or the like obtained by an arbitrary method, and cells obtained by inducing differentiation of pluripotent stem cells.

The term "extraction of cardiomyocytes" means that the ratio of cardiomyocytes is increased relative to other types of cells, and preferably means that the cardiomyocytes are concentrated to a ratio of not less than 50%, 60%, 70%, 80% or 90%. The term more preferably means that a cell population comprising cardiomyocytes at a ratio of 100% is obtained.

NCAM1 is the gene known as "neural cell adhesion molecule 1", CD56, NCAM or MSK39, and is involved in cell adhesion. For example, in the case of human, NCAM1 is the gene described in NCBI (National Center for Biotechnology Information) accession No. NM_000615, NM_001076682, NM_001242607 or NM_181351 or the protein encoded by thereby. NCAM1 also includes isoforms produced by alternative splicing.

SSEA3 and SSEA4 are epitopes on related glycosphingolipids (GSLs), termed GL-5 and GL-70, which are known as Anti-Stage-Specific Embryonic Antigen-3 and Anti-Stage-Specific Embryonic Antigen-4, respectively. Also, SSEA3 and SSEA4 are known to be recognized by MC631 antibody and MC813-70 antibody, respectively (Brimble S N et al., Stem Cells. 2007 January; 25(1):54-62.). Since SSEA3 and SSEA4 are specifically expressed on the surface of stem cells, these are generally used as stem cell markers.

CD340 is the member of the EGF receptor family known as "v-erb-b2 erythroblastic leukemia viral oncogene homolog 2" (ERBB2), HER-2/neu or the like. For example, in the case of human, CD340 is the gene described in NCBI (National Center for Biotechnology Information) accession No. NM_001005862 or NM_004448 or the protein encoded by thereby.

When cardiomyocytes are extracted from a cell population comprising cardiomyocytes using as an index NCAM1, SSEA3, SSEA4 and/or CD340, each of these genes or the proteins encoded thereby may be used alone, or two or more of these may be used in an arbitrary combination. In cases where NCAM1, SSEA3, SSEA4 and CD340 are used in combination, the concentration ratio of cardiomyocytes can be preferably increased compared to cases where each of these is used alone.

The term "cardiomyocyte" means a cell of a cardiac muscle having the property of self-beating. The cardiomyocyte can be characterized by being positive for cardiac troponin (cTnT or troponin T type 2) and/or αMHC (α myosin heavy chain), which are myocardial markers.

<Pluripotent Stem Cells>

The pluripotent stem cells which may be used in the present invention are stem cells having pluripotency which enables the cells to differentiate into any cells existing in the living body, which stem cells also have growth ability. Examples of the pluripotent stem cells include, but are not limited to, embryonic stem (ES) cells, embryonic stem cells derived from a cloned embryo obtained by nuclear transfer (ntES cells), germline stem cells ("GS cells"), embryonic germ cells ("EG cells") and induced pluripotent stem (iPS) cells. The pluripotent stem cells are preferably ES cells, ntES cells or iPS cells.

(A) Embryonic Stem Cells

ES cells are stem cells established from the inner cell mass of an early embryo (for example, blastocyst) of a mammal such as human or mouse, which cells have pluripotency and growth ability by self-renewal.

ES cells are embryo-derived stem cells originated from the inner cell mass of a blastocyst which is the embryo formed following the 8-cell stage and the morula stage of a fertilized egg, and ES cells have ability to differentiate into any cells constituting an adult, that is, the so called pluripotency of differentiation, and growth ability by self-renewal. ES cells were discovered in mouse in 1981 (M. J. Evans and M. H. Kaufman (1981), Nature 292:154-156), and this was followed by establishment of ES cell lines of primates such as human and monkey (J. A. Thomson et al. (1998), Science 282:1145-1147; J. A. Thomson et al. (1995), Proc. Natl. Acad. Sci. USA, 92:7844-7848; J. A. Thomson et al. (1996), Biol. Reprod., 55:254-259; J. A. Thomson and V. S. Marshall (1998), Curr. Top. Dev. Biol., 38:133-165).

ES cells can be established by removing the inner cell mass from the blastocyst of a fertilized egg of the subject animal, followed by culturing the inner cell mass on fibroblasts as feeders. The cells can be maintained by subculturing using a medium supplemented with substances such as leukemia inhibitory factor (LIF) and/or basic fibroblast growth factor (bFGF). Methods of establishment and maintenance of human and monkey ES cells are described in, for example, U.S. Pat. No. 5,843,780 B; Thomson J A, et al. (1995), Proc Natl. Acad. Sci. USA. 92:7844-7848; Thomson J A, et al. (1998), Science. 282:1145-1147; H. Suemori et al. (2006), Biochem. Biophys. Res. Commun., 345:926-932; M. Ueno et al. (2006), Proc. Natl. Acad. Sci. USA, 103: 9554-9559; H. Suemori et al. (2001), Dev. Dyn., 222:273-279; H. Kawasaki et al. (2002), Proc. Natl. Acad. Sci. USA, 99:1580-1585; and Klimanskaya I, et al. (2006), Nature. 444:481-485.

In terms of the medium for preparation of ES cells, human ES cells can be maintained, for example, using DMEM/F-12 medium supplemented with 0.1 mM 2-mercaptoethanol, 0.1 mM non-essential amino acids, 2 mM L-glutamic acid, 20% KSR and 4 ng/ml bFGF at 37° C. under a moist atmosphere of 2% $CO_2$/98% air (O. Fumitaka et al. (2008), Nat. Biotechnol., 26:215-224). Further, ES cells need to be subcultured every 3 to 4 days, and the subculture can be carried out using 0.25% trypsin and 0.1 mg/ml collagenase IV in PBS supplemented with 1 mM $CaCl_2$ and 20% KSR.

Selection of ES cells can be generally carried out by the Real-Time PCR method using as an index/indices expression of a gene marker(s) such as alkaline phosphatase, Oct-3/4 and/or Nanog. In particular, for selection of human ES cells, expression of a gene marker(s) such as OCT-3/4, NANOG and/or ECAD can be used as an index/indices (E. Kroon et al. (2008), Nat. Biotechnol., 26:443-452).

For example, in terms of human ES cell lines, WA01(H1) and WA09(H9) can be obtained from WiCell Research Institute, and KhES-1, KhES-2 and KhES-3 can be obtained from Institute for Frontier Medical Sciences, Kyoto University (Kyoto, Japan).

(B) Germline Stem Cells

Germline stem cells are pluripotent stem cells derived from testis, and play a role as the origin for spermatogenesis. Similarly to ES cells, these cells can be induced to differentiate into various series of cells, and, for example, have a property to enable preparation of a chimeric mouse by transplantation of the cells to a mouse blastocyst (M. Kanatsu-Shinohara et al. (2003) Biol. Reprod., 69:612-616; K. Shinohara et al. (2004), Cell, 119:1001-1012). Germline stem cells are capable of self-renewal in a medium containing glial cell line-derived neurotrophic factor (GDNF), and, by repeating subculture under the same culture conditions as those for ES cells, germline stem cells can be obtained (Masanori Takehashi et al. (2008), Experimental Medicine, 26(5) (extra edition):41-46, Yodosha (Tokyo, Japan)).

(C) Embryonic Germ Cells

Embryonic germ cells are established from fetal primordial germ cells and have pluripotency similar to that of ES cells. They can be established by culturing primordial germ cells in the presence of substances such as LIF, bFGF and stem cell factor (Y. Matsui et al. (1992), Cell, 70:841-847; J. L. Resnick et al. (1992), Nature, 359:550-551).

(D) Induced Pluripotent Stem Cells

Induced pluripotent stem (iPS) cells can be prepared by introducing specific reprogramming factors to somatic cells, which reprogramming factors are in the form of DNA or protein. iPS cells are somatic cell-derived artificial stem cells having properties almost equivalent to those of ES cells, such as pluripotency of differentiation and growth ability by self-renewal (K. Takahashi and S. Yamanaka (2006) Cell, 126:663-676; K. Takahashi et al. (2007), Cell, 131:861-872; J. Yu et al. (2007), Science, 318:1917-1920; Nakagawa, M. et al., Nat. Biotechnol. 26:101-106 (2008); WO 2007/069666). The reprogramming factors may be constituted by genes or gene products thereof, or non-coding RNAs, which are expressed specifically in ES cells; or genes or gene products thereof, non-coding RNAs or low molecular weight compounds, which play important roles in maintenance of the undifferentiated state of ES cells. Examples of the genes included in the reprogramming factors include Oct3/4, Sox2, Sox1, Sox3, Sox15, Sox17, Klf4, Klf2, c-Myc, N-Myc, L-Myc, Nanog, Lin28, Fbx15, ERas, ECAT15-2, Tcl1, beta-catenin, Lin28b, Sall1, Sall4, Esrrb, Nr5a2 and Tbx3, and these reprogramming factors may be used either individually or in combination. Examples of the combination of the reprogramming factors include those described in WO2007/069666; WO2008/118820; WO2009/007852; WO2009/032194; WO2009/058413; WO2009/057831; WO2009/075119; WO2009/079007; WO2009/091659; WO2009/101084; WO2009/101407; WO2009/102983; WO2009/114949; WO2009/117439; WO2009/126250; WO2009/126251; WO2009/126655; WO2009/157593; WO2010/009015; WO2010/033906; WO2010/033920; WO2010/042800; WO2010/050626; WO 2010/056831; WO2010/068955; WO2010/098419; WO2010/102267; WO 2010/111409; WO 2010/111422; WO2010/115050; WO2010/124290; WO2010/147395; WO2010/147612; Huangfu D, et al. (2008), Nat. Biotechnol., 26: 795-797; Shi Y, et al. (2008), Cell Stem Cell, 2: 525-528; Eminli S, et al. (2008), Stem Cells. 26:2467-2474; Huangfu D, et al. (2008), Nat Biotechnol. 26:1269-1275; Shi Y, et al. (2008), Cell Stem Cell, 3, 568-574; Zhao Y, et al. (2008), Cell Stem Cell, 3:475-479; Marson A, (2008), Cell Stem Cell, 3, 132-135; Feng B, et al. (2009), Nat Cell Biol. 11:197-203; R. L. Judson et al., (2009), Nat. Biotech., 27:459-461; Lyssiotis C A, et al. (2009), Proc Natl Acad Sci USA. 106:8912-8917; Kim J B, et al. (2009), Nature. 461:649-643; Ichida J K, et al. (2009), Cell Stem Cell. 5:491-503; Heng J C, et al. (2010), Cell Stem Cell. 6:167-74; Han J, et al. (2010), Nature. 463:1096-100; and Mali P, et al. (2010), Stem Cells. 28:713-720.

Examples of the above-described reprogramming factors also include histone deacetylase (HDAC) inhibitors [for example, low molecular weight inhibitors such as valproic acid (VPA), trichostatin A, sodium butyrate, MC 1293 and M344; and nucleic acid-type expression inhibitors such as siRNAs and shRNAs against HDAC (e.g., HDAC1 siRNA Smartpool® (Millipore) and HuSH 29mer shRNA Constructs against HDAC1 (OriGene))], MEK inhibitors (for example, PD184352, PD98059, U0126, SL327 and PD0325901), Glycogen synthase kinase-3 inhibitors (for example, Bio and CHIR99021), DNA methyltransferase inhibitors (for example, 5'-azacytidine), histone methyltransferase inhibitors (for example, low molecular weight inhibitors such as BIX-01294; and nucleic acid-type expression inhibitors such as siRNAs and shRNAs against Suv39h1, Suv39h2, SetDB1 and G9a), L-channel calcium agonists (for example, Bayk8644), butyric acid, TGFβ inhibitors or ALK5 inhibitors (for example, LY364947, SB431542, 616453 and A-83-01), p53 inhibitors (for example, siRNAs and shRNAs against p53), ARID3A inhibitors (for example, siRNAs and shRNAs against ARID3A), miRNAs such as miR-291-3p, miR-294, miR-295 and mir-302, Wnt Signaling (for example, soluble Wnt3a), neuropeptide Y, prostaglandins (for example, prostaglandin E2 and prostaglandin J2), hTERT, SV40LT, UTF1, IRX6, GLIS1, PITX2 and DMRTB1, which are employed for enhancing the establishment efficiency, and, in the present description, these factors employed for the purpose of enhancement of the establishment efficiency are not particularly distinguished from reprogramming factors.

In cases where the reprogramming factors are in the form of protein, the reprogramming factors may be introduced into somatic cells by a method such as lipofection, fusion with a cell-permeable peptide (e.g., HIV-derived TAT or polyarginine), or microinjection.

In cases where the reprogramming factors are in the form of DNA, the reprogramming factors may be introduced into somatic cells by a method such as use of a vector including virus, plasmid and artificial chromosome vectors; lipofection; use of liposome; or microinjection. Examples of the virus vector include retrovirus vectors, lentivirus vectors (these are described in Cell, 126, pp. 663-676, 2006; Cell, 131, pp. 861-872, 2007; and Science, 318, pp. 1917-1920, 2007), adenovirus vectors (Science, 322, 945-949, 2008), adeno-associated virus vectors and Sendai virus vectors (WO 2010/008054). Examples of the artificial chromosome vector include human artificial chromosome (HAC), yeast artificial chromosome (YAC), and bacterial artificial chromosome (BAC and PAC). Examples of the plasmid which may be used include plasmids for mammalian cells (Science, 322:949-953, 2008). The vector may contain a regulatory sequence(s) such as a promoter, enhancer, ribosome binding sequence, terminator and/or polyadenylation site to enable expression of the nuclear reprogramming factors; and, as required, a sequence of a selection marker such as a drug resistance gene (e.g., kanamycin-resistant gene, ampicillin-resistant gene or puromycin-resistant gene), thymidine kinase gene or diphtheria toxin gene; a gene sequence of a reporter such as the green-fluorescent protein (GFP), β-glucuronidase (GUS) or FLAG; and/or the like. Further, in order to remove, after introduction of the above vector into somatic cells, the genes encoding the reprogramming factors, or both the promoter(s) and the genes encoding the reprogramming factors linked thereto, the vector may have LoxP sequences upstream and downstream of these sequences.

Further, in cases where the reprogramming factors are in the form of RNA, each reprogramming factor may be introduced into somatic cells by a method such as lipofection or microinjection, and an RNA into which 5-methylcytidine and pseudouridine (TriLink Biotechnologies) were incorporated may be used in order to suppress degradation (Warren L, (2010) Cell Stem Cell. 7:618-630).

Examples of the medium for induction of the iPS cells include the DMEM, DMEM/F12 and DME media supplemented with 10 to 15% FBS (these media may further contain LIF, penicillin/streptomycin, puromycin, L-glutamine, non-essential amino acids, β-mercaptoethanol and/or the like, as appropriate); and commercially available media [for example, medium for culturing mouse ES cells (TX-WES medium, Thromb-X), medium for culturing primate ES cells (medium for primate ES/iPS cells, ReproCELL) and serum-free medium (mTeSR, Stemcell Technology)].

Examples of the culture method include a method wherein somatic cells and reprogramming factors are brought into contact with each other at 37° C. in the presence of 5% $CO_2$ on DMEM or DMEM/F12 medium supplemented with 10% FBS, and the cells are cultured for about 4 to 7 days, followed by plating the cells on feeder cells (e.g., mitomycin C-treated STO cells or SNL cells) and starting culture in a bFGF-containing medium for culturing primate ES cells about 10 days after the contact between the somatic cells and the reprogramming factors, thereby allowing iPS-like colonies to appear about 30 to about 45 days after the contact, or later.

Alternatively, the cells may be cultured at 37° C. in the presence of 5% $CO_2$ on feeder cells (e.g., mitomycin C-treated STO cells or SNL cells) in DMEM medium supplemented with 10% FBS (this medium may further contain LIF, penicillin/streptomycin, puromycin, L-glutamine, non-essential amino acids, β-mercaptoethanol and/or the like, as appropriate) for about 25 to about 30 days or longer, thereby allowing ES-like colonies to appear. Preferred examples of the culture method include a method wherein the somatic cells themselves to be reprogrammed are used instead of the feeder cells (Takahashi K, et al. (2009), PLoS One. 4:e8067 or WO2010/137746), and a method wherein an extracellular matrix (e.g., Laminin-5 (WO2009/123349) or Matrigel (BD)) is used instead.

Other examples include a method wherein the culture is carried out using a serum-free medium (Sun N, et al. (2009), Proc Natl Acad Sci USA. 106:15720-15725). Further, in order to enhance the establishment efficiency, iPS cells may be established under low oxygen conditions (at an oxygen concentration of 0.1% to 15%) (Yoshida Y, et al. (2009), Cell Stem Cell. 5:237-241 or WO2010/013845).

During the culture, the medium is replaced with a fresh medium once every day from Day 2 of the culture. The number of somatic cells used for nuclear reprogramming is not restricted, and usually within the range of about $5 \times 10^3$ to about $5 \times 10^6$ cells per 100-$cm^2$ area on the culture dish.

iPS cells may be selected based on the shape of each formed colony. In cases where a drug resistance gene is introduced as a marker gene such that the drug resistance gene is expressed in conjunction with a gene that is expressed when a somatic cell was reprogrammed (e.g., Oct3/4 or Nanog), the established iPS cells can be selected by culturing the cells in a medium containing the corresponding drug (selection medium). Further, iPS cells can be selected by observation under a fluorescence microscope in cases where the marker gene is the gene of a fluorescent protein; by adding a luminescent substrate in cases where the marker gene is the gene of luciferase; or by adding a coloring substrate in cases where the marker gene is the gene of a coloring enzyme.

The term "somatic cells" used in the present description means any animal cells (preferably cells of a mammal including human) excluding germ-line cells and totipotent cells such as eggs, oocytes and ES cells. Examples of the somatic cells include, but are not limited to, any of fetal somatic cells, neonatal somatic cells, and mature, healthy and diseased somatic cells, as well as any of primary cultured cells, subcultured cells and established cell lines. Specific examples of the somatic cells include (1) tissue stem cells (somatic stem cells) such as neural stem cells, hematopoietic stem cells, mesenchymal stem cells and dental pulp stem cells; (2) tissue progenitor cells; and (3) differentiated cells such as lymphocytes, epithelial cells, endothelial cells, muscle cells, fibroblasts (skin cells and the like), hair cells, hepatic cells, gastric mucosal cells, enterocytes, spleen cells, pancreatic cells (pancreatic exocrine cells and the like), brain cells, lung cells, kidney cells and adipocytes.

In cases where iPS cells are used as a material for the cells to be transplanted, somatic cells having the same or substantially the same HLA genotype as that of the individual to which the cells are to be transplanted are preferably used in view of prevention of the rejection reaction. Here, "substantially the same" means that the HLA genotype is matching to an extent at which the immune reaction against the transplanted cells can be suppressed with an immunosuppressive agent. For example, the somatic cells have matched HLA types at 3 loci, HLA-A, HLA-B and HLA-DR, or at 4 loci further including HLA-C.

(E) ES Cells Derived from Cloned Embryo Obtained by Nuclear Transfer ntES cells are ES cells derived from a cloned embryo prepared by the nuclear transfer technique, and have properties which are almost the same as those of ES cells derived from fertilized eggs (T. Wakayama et al. (2001), Science, 292:740-743; S. Wakayama et al. (2005), Biol. Reprod., 72:932-936; J. Byrne et al. (2007), Nature, 450:497-502). That is, an ntES (nuclear transfer ES) cell is an ES cell established from the inner cell mass of a blastocyst derived from a cloned embryo obtained by replacement of the nucleus of an unfertilized egg with the nucleus of a somatic cell. For preparation of an ntES cell, the combination of the nuclear transfer technique (J. B. Cibelli et al. (1998), Nature Biotechnol., 16:642-646) and the ES cell preparation technique (described above) is employed (Sayaka Wakayama et al. (2008), Experimental Medicine 26(5) (extra edition):47-52). In nuclear transfer, reprogramming can be achieved by injecting the nucleus of a somatic cell into a mammalian enucleated unfertilized egg and culturing the resultant for several hours.

<Method for Preparing Cardiomyocytes from Pluripotent Stem Cells>

The method for inducing differentiation of pluripotent stem cells into cardiomyocytes is not restricted, and, for example, the following method may be Pluripotent stem cells may be separated by an arbitrary method and subjected to suspension culture, or adherent culture using a coated culture dish. In the method of separation, the cells may be mechanically separated, or may be separated using an EDTA solution (e.g., 0.5 mM EDTA solution or Versene (Invitrogen)), separation solution having protease activity and collagenase activity (e.g., Accutase™ or Accumax™), or separation solution having only collagenase activity. In the suspension culture, the culture dish may have either a surface which is not subjected to artificial treatment for the purpose of enhancing adhesiveness to cells such as coating treatment with an extracellular matrix or the like, or a surface which is artificially treated such that adhesion is suppressed (for example, by coating treatment with polyhydroxyethylmethacrylate (poly-HEMA). In the adherent culture, the culture dish may be one coated with Matrigel (BD), type I collagen, type IV collagen, gelatin, laminin, heparan sulfate proteoglycan or entactin, or a combinations thereof.

The suspension culture and the adherent culture may be performed in combination. In an embodiment of the present invention where these are performed in combination, the suspension culture may be followed by adherent culture without any treatment, or mesodermal cells prepared by the suspension culture may be selected before the adherent culture. In the present description, "mesoderm" includes germ layers constituted by cells capable of producing, during development, the body cavity and mesothelium lining it, muscles, skeletons, dermis, connective tissues, heart/blood vessels (including vascular endothelium), blood (including blood cells), lymph vessels and spleen, kidney and ureter, and gonads (testis, uterus and gonadal epithelium). These can be detected by expression of markers such as T, KDR, FOXF1, FLK1 and/or BMP4. The cells preferably express KDR or FLK1.

The adherent culture may be carried out by co-culture with feeder cells. Examples of the feeder cells to be used in the co-culture include OP9 cells (Nishikawa, S. I. et al., Development 125, 1747-1757 (1998)) and END-2 cells (Mummery C, et al., Circulation. 107:2733-40 (2003)), but, in cases where the cultured cells are used as a material for cells to be transplanted, co-culture is preferably avoided in view of prevention of contamination with other types of cells.

In another mode, embryoid bodies (EBs) are formed from pluripotent stem cells isolated by an arbitrary method, and then subjected to adherent culture in an arbitrary medium in a coated culture dish. In other mode, EBs are formed from pluripotent stem cells isolated by an arbitrary method, and then subjected to adherent culture in an arbitrary medium in a coated culture dish, followed by again the formation of EBs. By these, cardiomyocytes can be induced. The EBs are usually formed by suspension culture, but the mode is not limited thereto.

In this process, the medium may be prepared using, as a basal medium, a medium for use in animal cell culture. Examples of the basal medium include IMDM medium, Medium 199, Eagle's Minimum Essential Medium (EMEM), α-MEM medium, Dulbecco's modified Eagle's Medium (DMEM), Ham's F12 medium, RPMI 1640 medium and Fischer's medium, and mixtures thereof. The medium is preferably StemPro 34 medium. The medium may either contain serum or be serum-free. The culture medium may also contain, as required, one or more of serum replacements such as albumin, transferrin, Knockout Serum Replacement (KSR) (serum replacement for FBS in ES cell culture), fatty acids, insulin, collagen precursors, trace elements, 2-mercaptoethanol, 3'-thiolglycerol and ITS-supplements; and/or one or more of substances such as B27 supplement, N2 supplement, lipids, amino acids, L-glutamic acid, Glutamax (Invitrogen), non-essential amino acids, vitamins, growth factors, cytokines, Wnt inhibitors, antibiotics, antioxidants, pyruvic acid, buffers and inorganic salts. Examples of the cytokines include activin A, BMP4, b-FGF, and VEGF. Examples of Wnt inhibitors include DKK1 (NCBI Accession No. NM_012242 in human), and Sclerostin (NCBI Accession No. NM_025237 in human)IWR-1 (Merck Millipore), IWP-2 (Sigma-Aldrich), IWP-3 (Sigma-Aldrich), IWP-4 (Sigma-Aldrich), PNU-74654 (Sigma-Aldrich), XAV939 (Sigma-Aldrich), and derivatives thereof.

In cases where the substances described above are added to the medium, different agents may be added at each stage of culture. The concentrations of the substances may be arbitrarily set depending on the type of the cells to which the agents are applied.

The culture temperature is not restricted and may be about 30 to 40° C., preferably about 37° C., and the culture is carried out under an atmosphere of $CO_2$-containing air wherein the $CO_2$ concentration is preferably about 2 to 5%. The culture is carried out for a number of days required for cardiac troponin and/or αMHC to be expressed, and the culturing period is, for example, not less than 8 days.

Induction of differentiation into cardiomyocytes may be carried out under low oxygen conditions. The oxygen concentration in the low oxygen conditions is, for example, 1 to 10%, preferably 5%, but the concentration is not limited thereto. The period under low oxygen conditions is not limited as long as induction of differentiation into cardiomyocytes can be achieved therewith, and may be, for example, 1 to 20 days, preferably 12 days.

For example, the method for producing cardiomyocytes from pluripotent stem cells is carried out under low oxygen conditions where pluripotent stem cells are cultured in StemPro 34 supplemented with BMP4 and ROCK inhibitor for 24 hours to allow formation of EBs, followed by 3 days of culture in a medium supplemented with activin A, BMP4 and bFGF, 4 days of culture in a medium supplemented with VEGF and DKK-1, and then several days of culture in a medium supplemented with VEGF and b-FGF. The last culture step may be carried out for an arbitrary period in order to evaluate the cells using a cardiomyocyte marker(s).

The thus produced cardiomyocytes may be either a population constituted by a single type cells, or may be a cell population that also comprises another type of cells.

<Method for Extraction or Detection of Cardiomyocytes>

For extraction or detection of cardiomyocytes from a cell population containing cardiomyocytes, any reagent having specific affinity to NCAM1, SSEA3, SSEA4 or CD340 may be used, and, for example, an antibody, aptamer, peptide or compound that specifically recognizes such a protein may be used. The reagent is preferably an antibody or a fragment thereof.

The antibody may be either a polyclonal antibody or a monoclonal antibody. These antibodies may be prepared using a technique well known to those skilled in the art (Current protocols in Molecular Biology edit. Ausubel et al. (1987) Publish. John Wiley and Sons. Section 11.12-11.13). More specifically, in cases where the antibody is a polyclonal antibody, a protein encoded by NCAM1, SSEA3, SSEA4 or CD340 which was expressed in E. coli or the like and purified according to a conventional method, or a synthetic oligopeptide having a partial amino acid sequence of the protein, may be used to immunize a nonhuman animal such as a rabbit, followed by obtaining the antibody from serum of the immunized animal according to a conventional method. On the other hand, the monoclonal antibody can be obtained from hybridoma cells prepared by cell fusion of spleen cells obtained from the above-described immunized nonhuman animal with myeloma cells (Current protocols in Molecular Biology edit. Ausubel et al. (1987) Publish. John Wiley and Sons. Section 11.4-11.11). Examples of the fragment of the antibody include parts (for example, the Fab fragment) of the antibody and synthetic antibody fragments (for example, the single-chain Fv fragment "ScFv"). Antibody fragments such as Fab and $F(ab)_2$ may also be prepared according to methods well known in the field of genetic engineering.

In order to distinguish and separate cells to which the reagent having affinity is bound, the reagent may be bound or conjugated to a detectable substance such as a fluorescent label, radioactive label, chemiluminescent label, enzyme, biotin or streptavidin, or to a substance that enables isolation and extraction of the cells, such as protein A, protein G, beads or magnetic beads.

The reagent having affinity may also be indirectly labeled. The labeling can be carried out by various methods known to those skilled in the art, and examples of the methods include a method using a preliminarily labeled antibody (secondary antibody) that specifically binds to an antibody against NCAM1, SSEA3, SSEA4 or CD340.

Examples of the method for detecting cardiomyocytes include flow cytometry and a method wherein the cells are isolated and purified, followed by detection of the cells (for example, using a protein chip).

Examples of the method for extracting cardiomyocytes include a method wherein a large particle is conjugated to the reagent having affinity to cause precipitation, a method wherein cells are sorted using magnetic beads by the magnetism (e.g., MACS), a method wherein a fluorescent label is used to employ a cell sorter, and a method wherein a carrier to which an antibody or the like is immobilized (e.g., cell-concentrating column) is used.

The present invention will now be described more concretely by way of Examples below, but the present invention is not restricted to these Examples.

EXAMPLES

Example 1

Preparation of Pluripotent Stem Cells

The 201B7-M6GIP4 strain and the 606A1 strain, which show cardiomyocyte-specific expression of EGFP, were prepared as described below. The 201B7-M6GIP4 strain and the 606A1 strain were cultured by a conventional method (Takahashi K, et al. Cell. 131: 861-72, 2007 and Nakagawa M, et al. Nat Biotechnol. 26: 101-6, 2008).

(1) 201B7-M6GIP4 Strain

OCT3/4, SOX2, KLF4 and C-MYC were introduced to human fibroblasts using a retrovirus, and the resulting cells were cultured on mitomycin-treated SNL feeder cells to establish iPS cells (201B7 strain). The promoter region of the human MYH6 gene and a sequence of the EGFP gene were introduced to the resulting 201B7 strain, to prepare a cell line (201B7-M6GIP4 strain). The 201B7-M6GIP4 strain has been confirmed to show cardiomyocyte-specific expression of GFP after induction of differentiation.

(2) 606A1 Strain

An episomal vector set (pCXLE-hOct3/4-shp53-F, pCXLE-hSK and pCXLE-hUL) that expresses OCT3/4, SOX2, KLF4, LIN28, L-MYC and p53 shRNAi was introduced to human umbilical cord blood cells by electroporation, and the resulting cells were cultured on mitomycin-treated mouse embryonic fibroblast feeders, to prepare an iPS cell line (606A1 strain).

The above-described cells of (1) and (2) were cultured on a 6-cm dish to 80 to 90% confluence. The feeder cells were removed, and the cultured cells were plated on a Matrigel-coated dish using trypsin/EDTA and cultured for additional 3 to 4 days. The cells were then detached by addition of collagenase B and a trypsin/EDTA solution.

Example 2

Method for Induction of Cardiomyocytes

The human iPS cells were plated on a dish at a density of 1.5 to $2.0 \times 10^6$ cells per well, and cultured under low oxygen conditions (5%) in StemPro 34 medium supplemented with 10 ng/ml BMP4 and 10 μM ROCK inhibitor for 24 hours to allow formation of EBs. On the following day, the medium was replaced with a medium supplemented with 6 ng/ml activin A (R & D Systems), 10 ng/ml BMP4 (R & D Systems) and 5 ng/ml bFGF (R & D Systems), and the culture was further continued for 3 days. Subsequently, the medium was replaced with a medium supplemented with 10 ng/ml VEGF (R & D Systems) and 150 ng/ml DKK-1 (R & D Systems), and the culture was further continued for 4 days. The medium was then replaced with a medium supplemented with 10 ng/ml VEGF (R & D Systems) and 5 ng/ml bFGF (R & D Systems), and the culture was further continued for 52 days. The cells at each step of differentiation from the iPS cells into cardiomyocytes were evaluated with the cardiomyocyte markers described below.

Example 3

Evaluation of Cells with Cardiomyocyte Marker NCAM1

Figure 3:
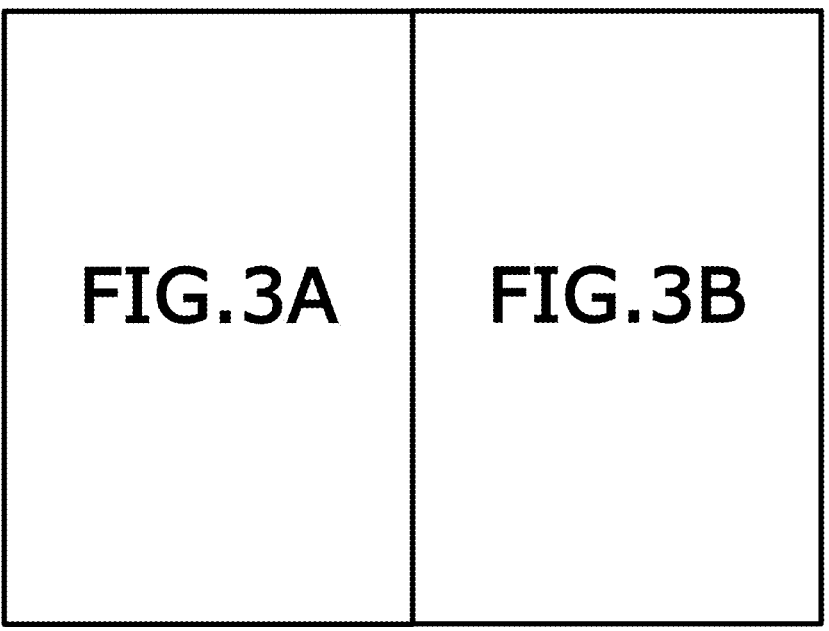
FIGS. 3A-3B illustrate the results of flow cytometry on Day 30 after the beginning of induction of differentiation of the 606A1 strain. In the left column, the abscissa indicates the intensity of NCAM1, and, in the right column, the abscissa indicates the intensity of Troponin T.
Figure 3A:
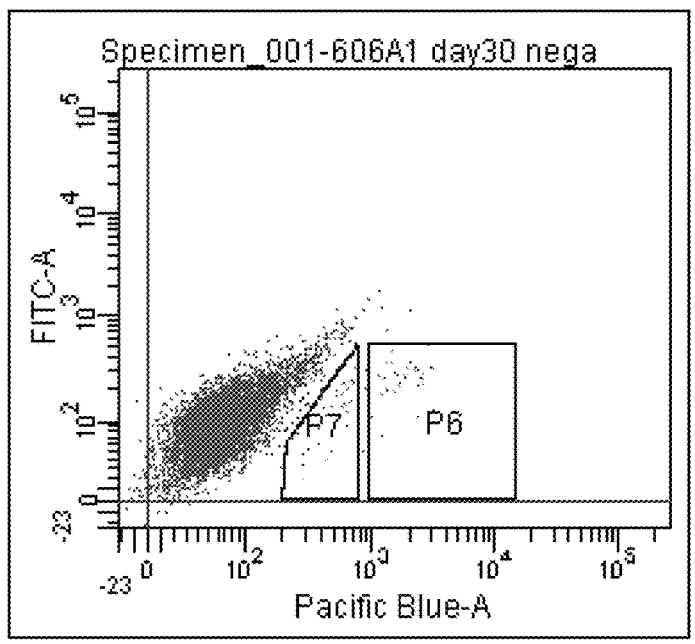
Figure 3A:
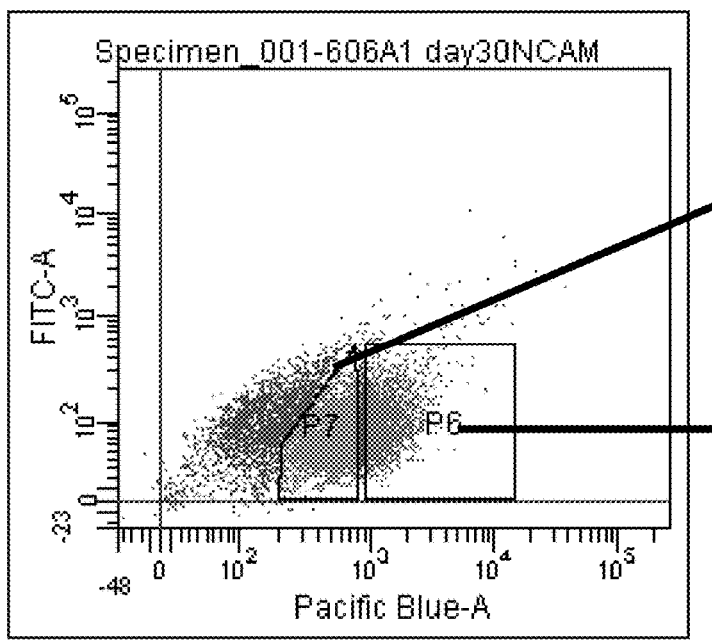
Figure 3B:
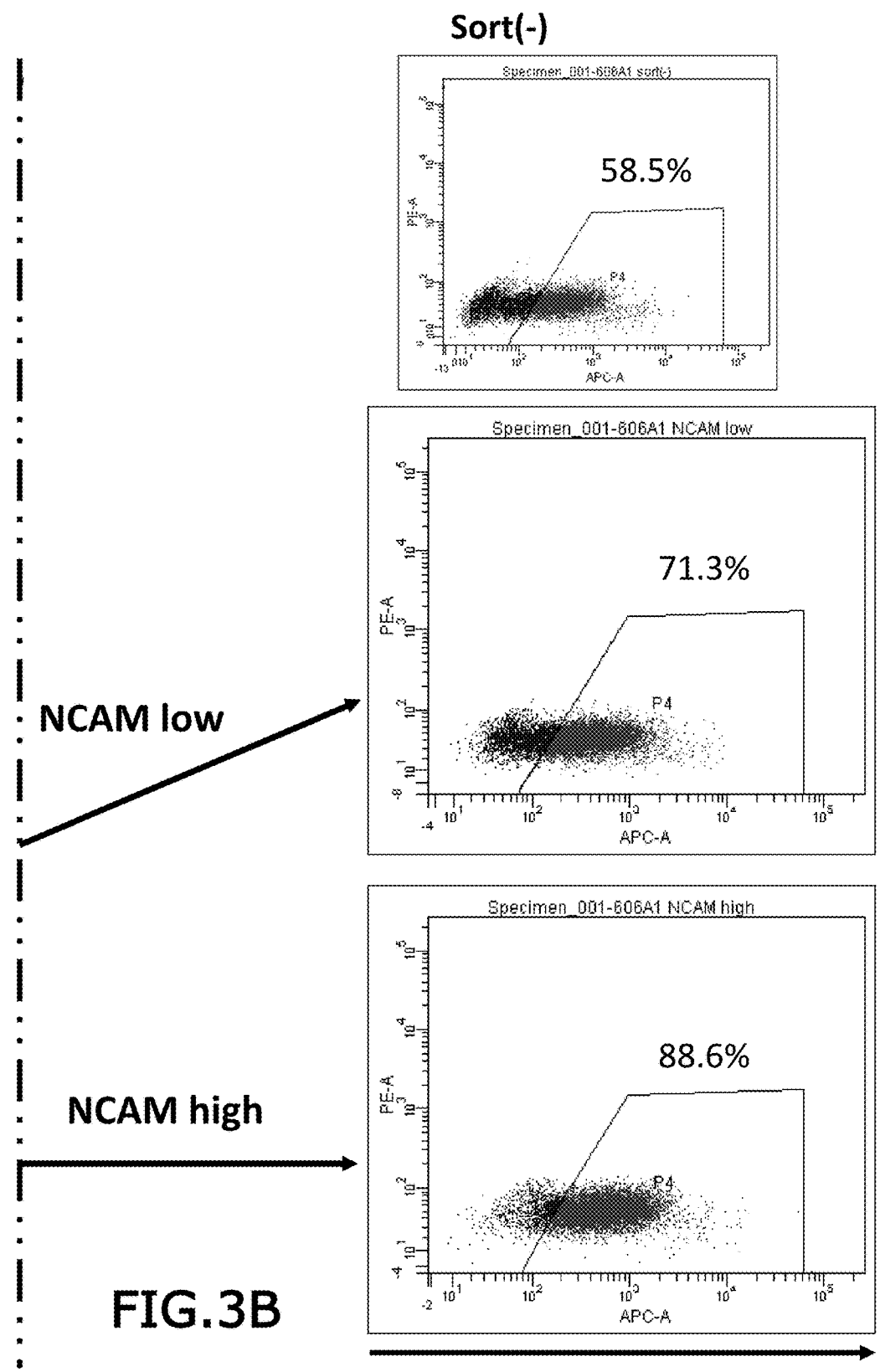
Figure 4A:
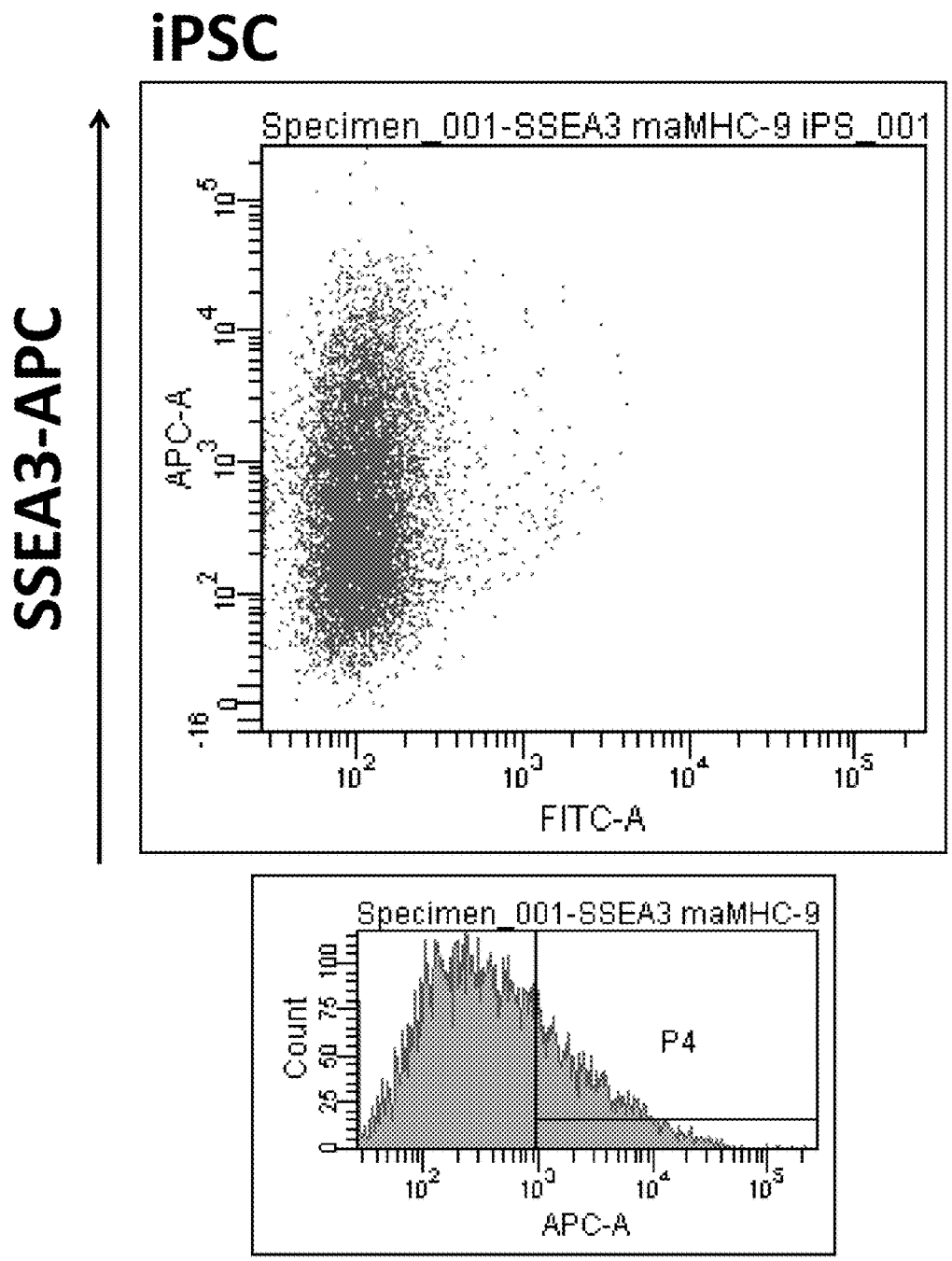
FIGS. 4A-4J illustrate the result of flow cytometry on Day 0 (FIG. 4A), Day 4 (FIG. 4B), Day 8 (FIG. 4C), Day 12 (FIG. 4D), Day 16 (FIG. 4E), Day 20 (FIG. 4F), Day 26 (FIG. 4G), Day 33 (FIG. 4H), Day 45 (FIG. 4I) and Day 60 (FIG. 4J) after the beginning of induction of differentiation of the 201B7-M6GIP4 strain.
Figure 4B:
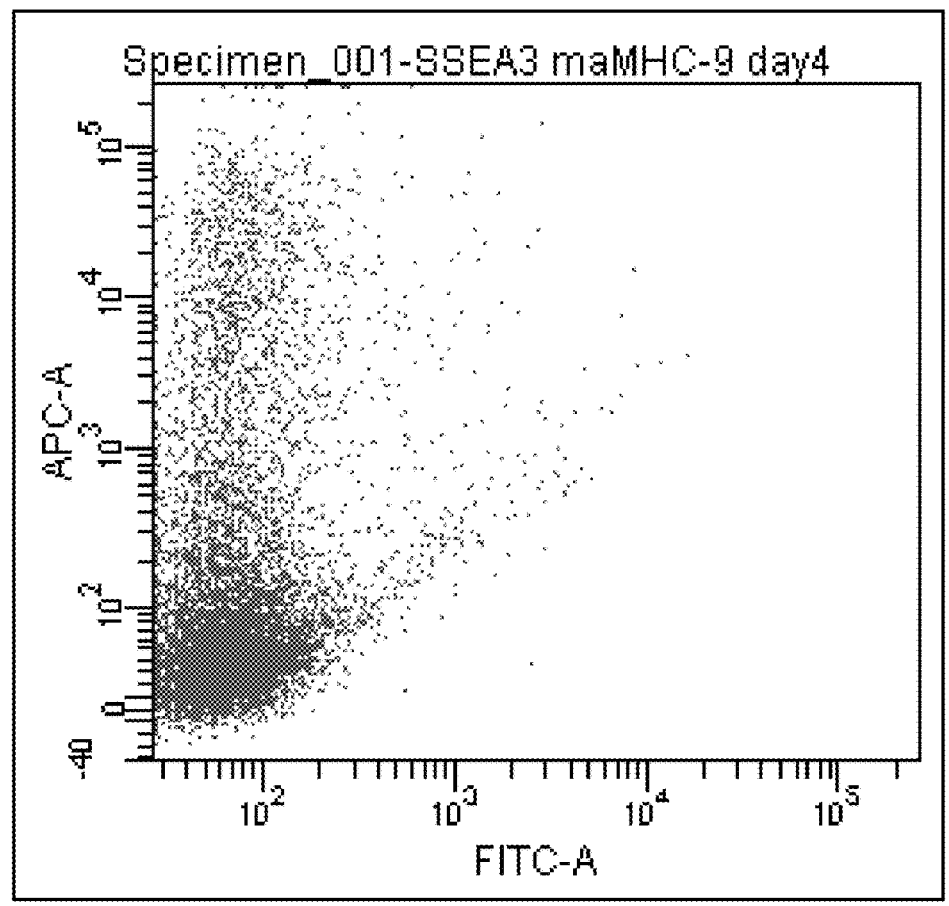
Figure 4B:
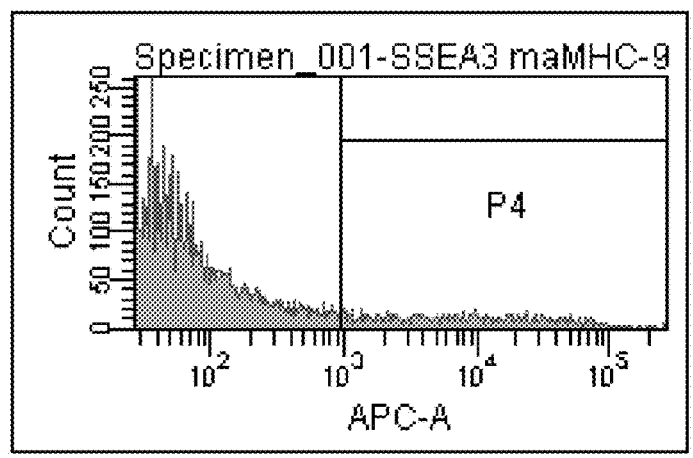
Figure 4C:
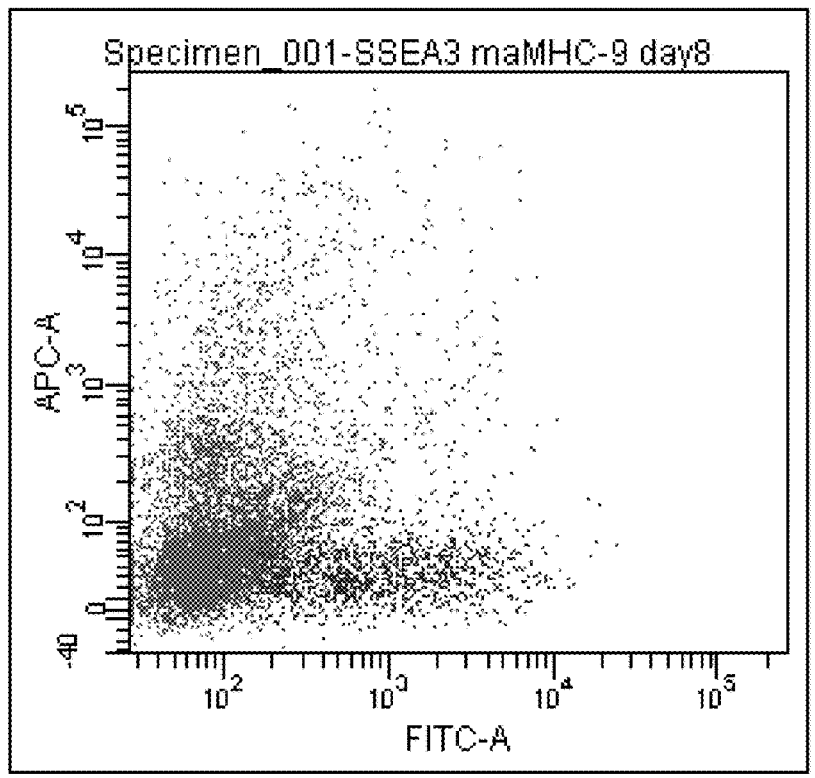
Figure 4C:
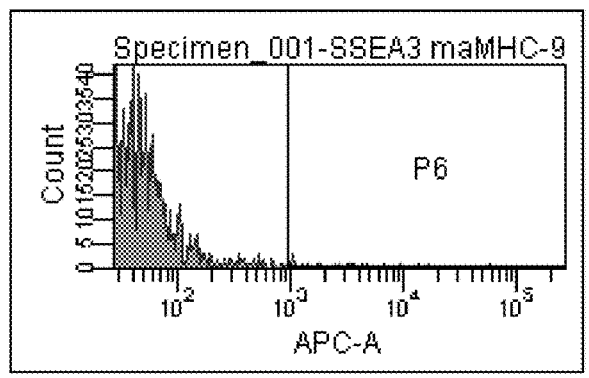
Figure 4C:
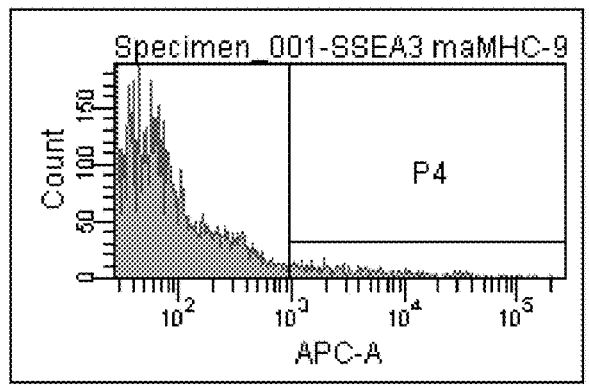
Figure 4D:
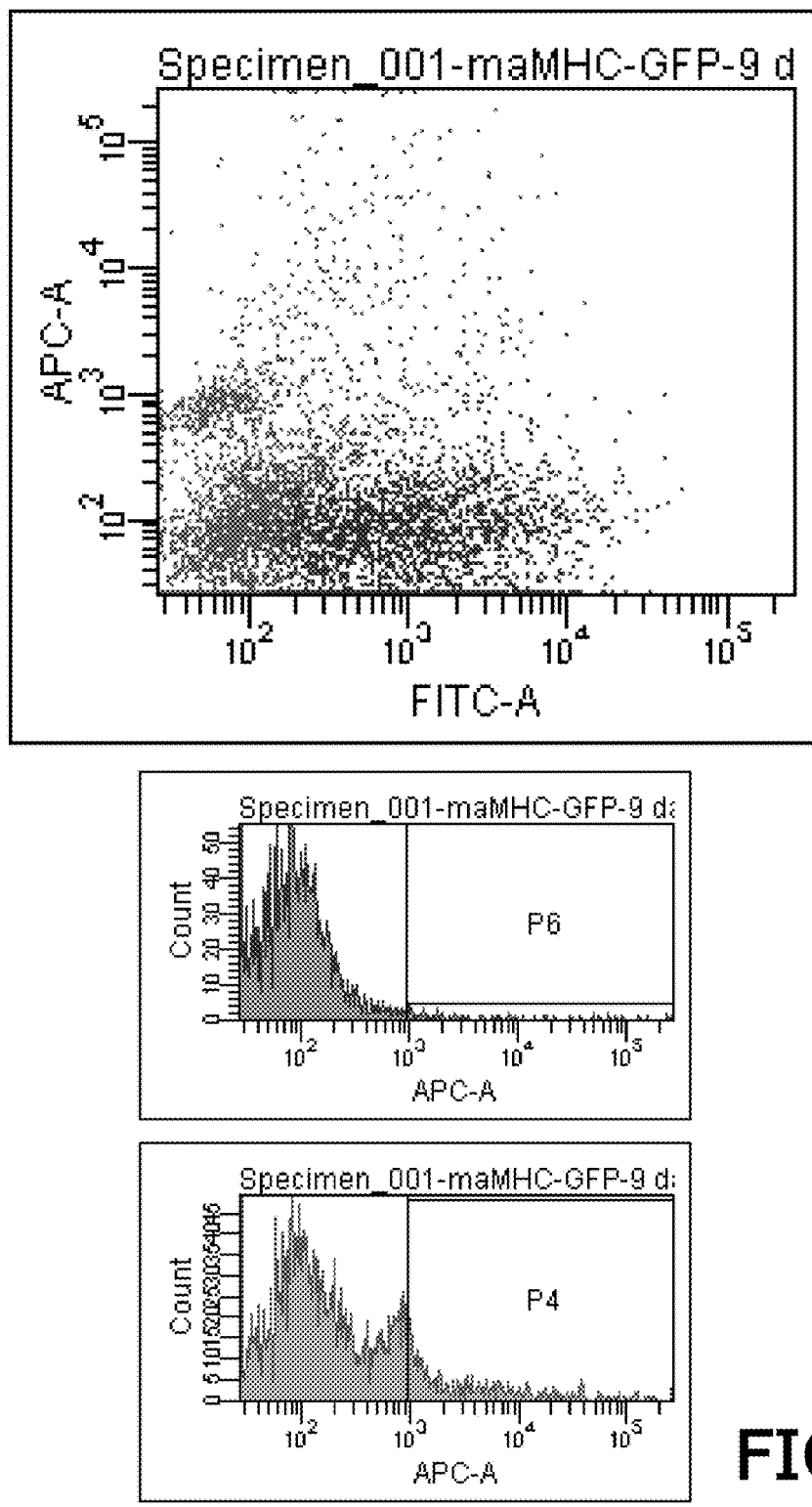
Figure 4E:
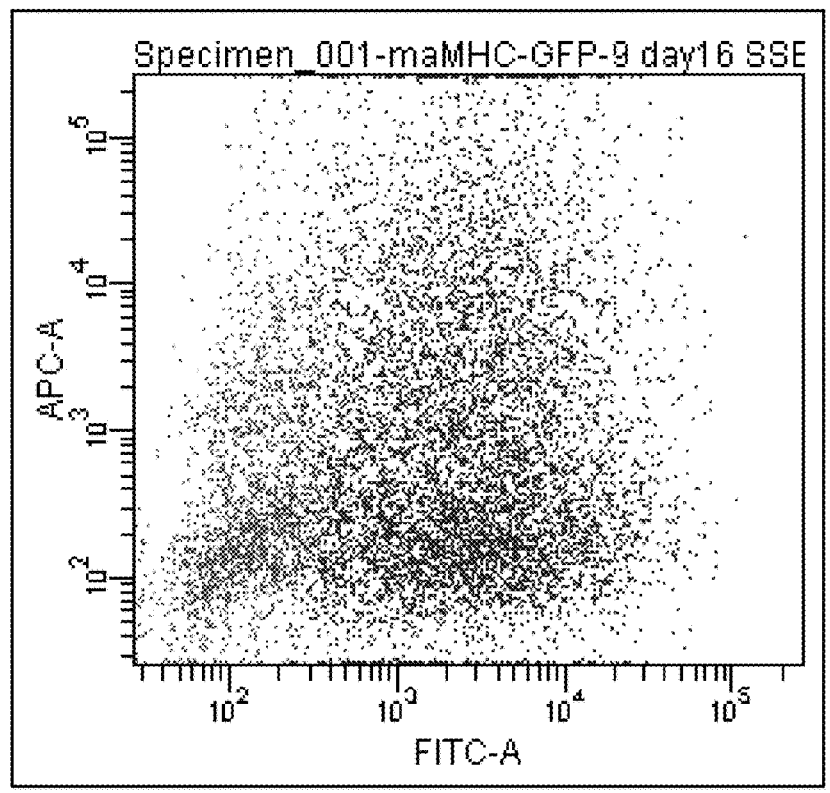
Figure 4E:
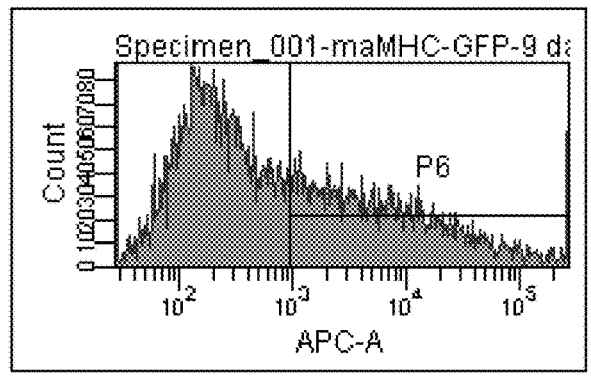
Figure 4E:
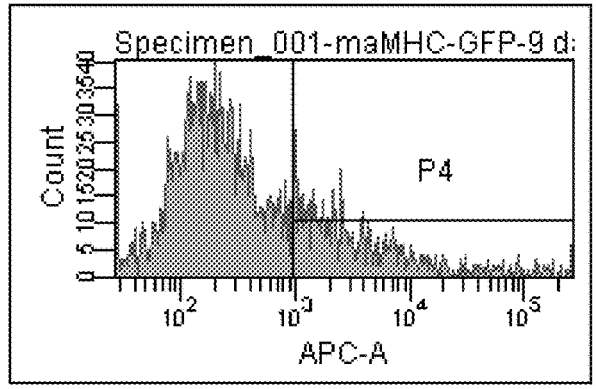
Figure 4F:
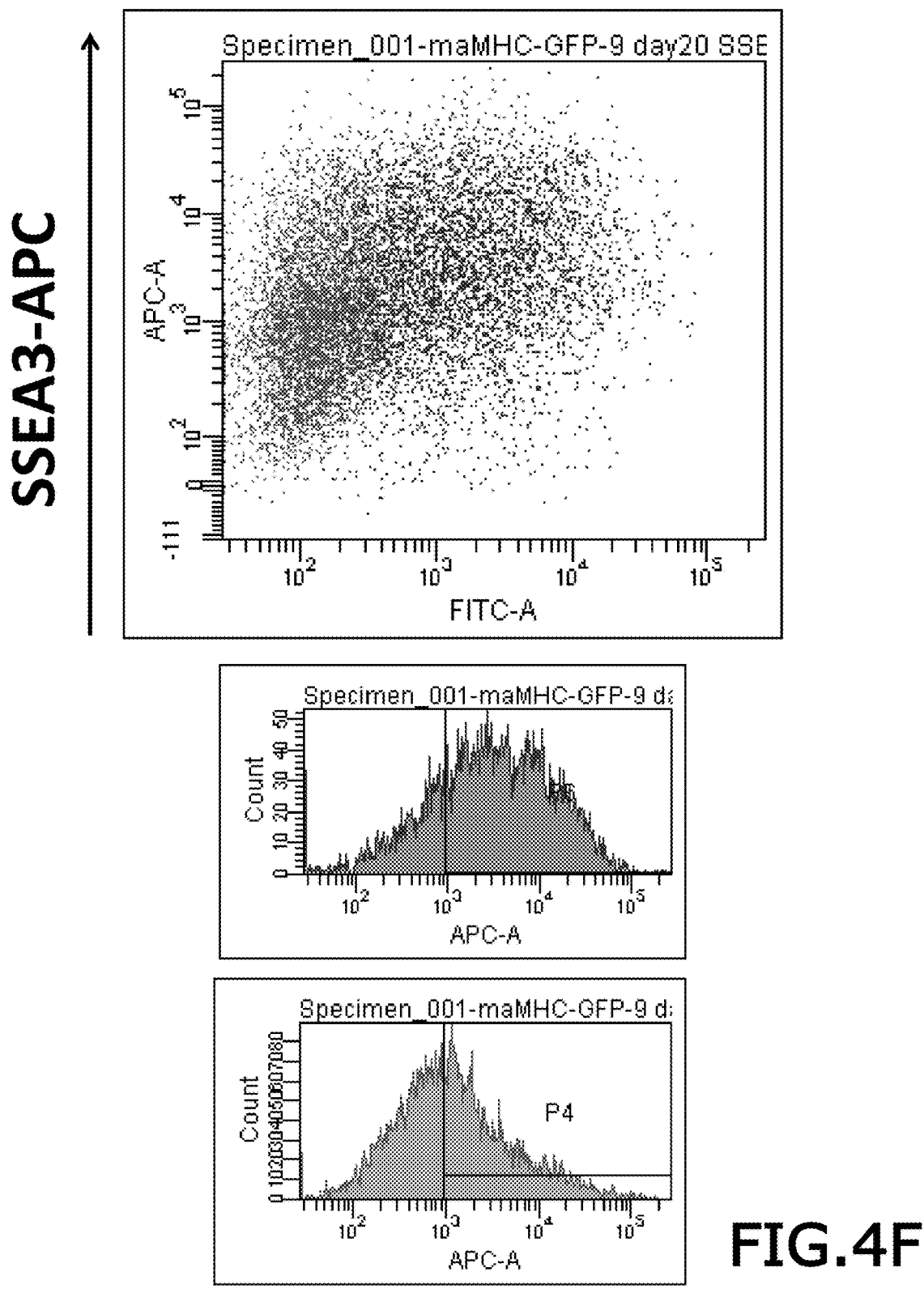
Figure 4G:
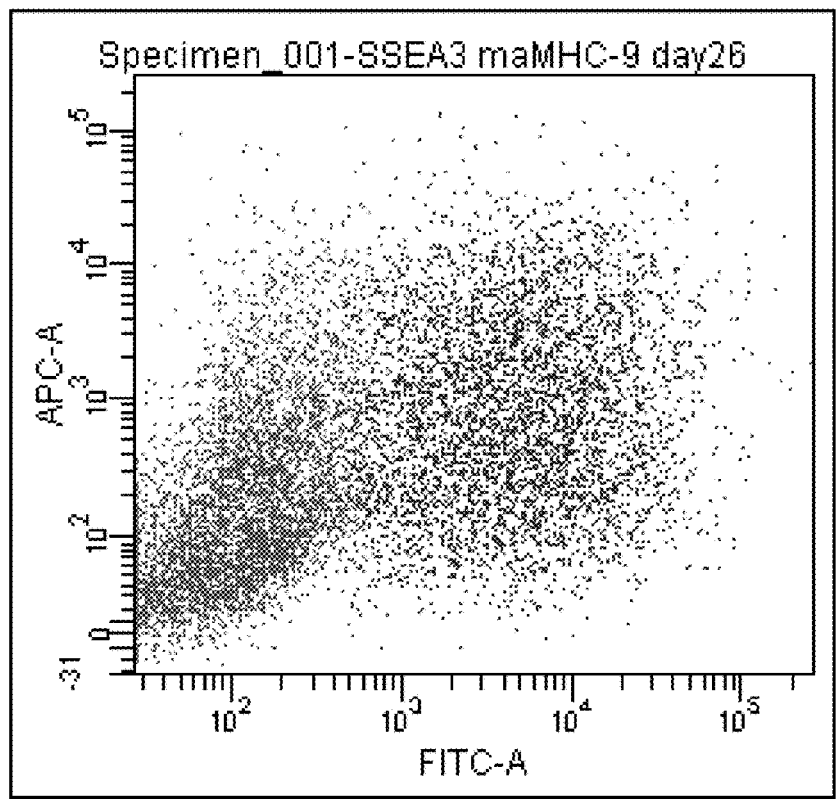
Figure 4G:
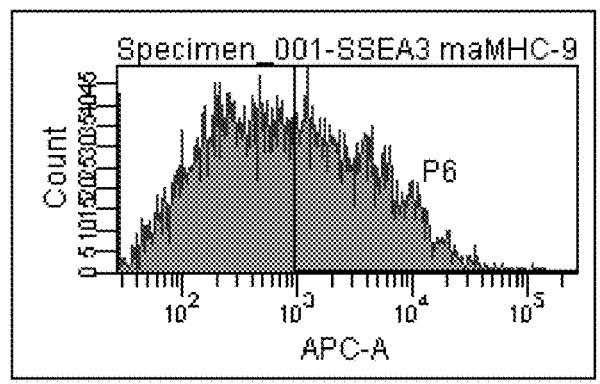
Figure 4G:
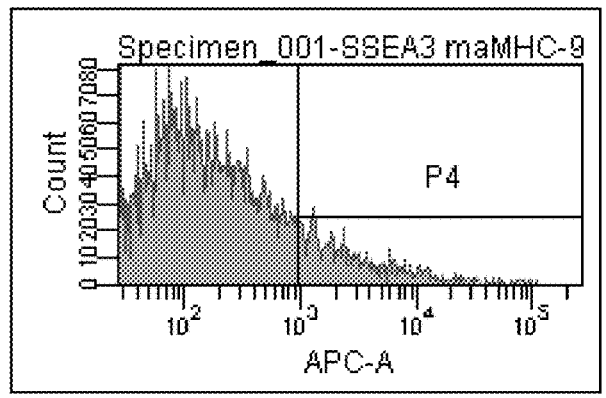
Figure 4H:
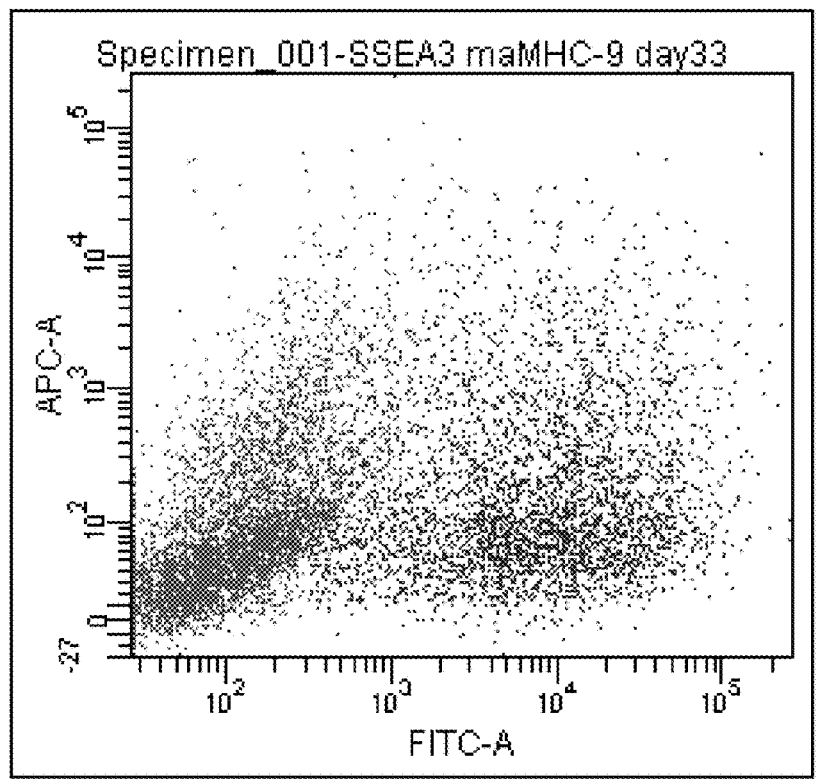
Figure 4H:
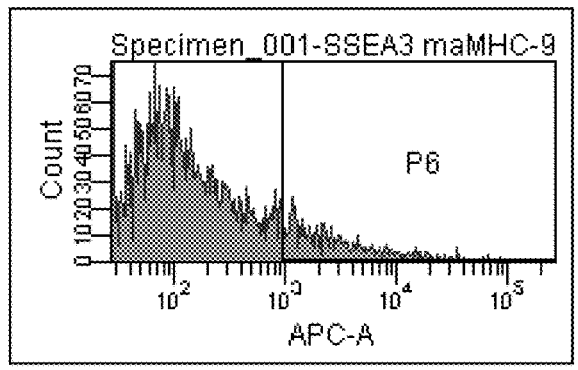
Figure 4H:
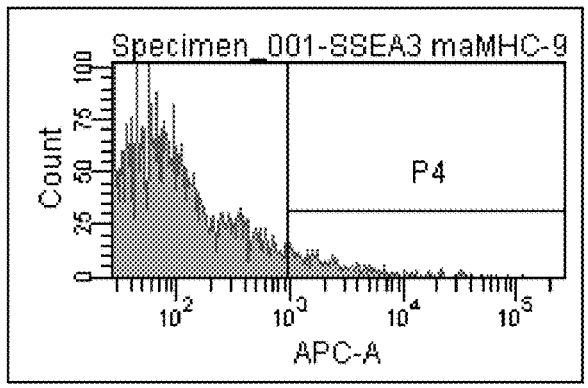
Figure 4I:
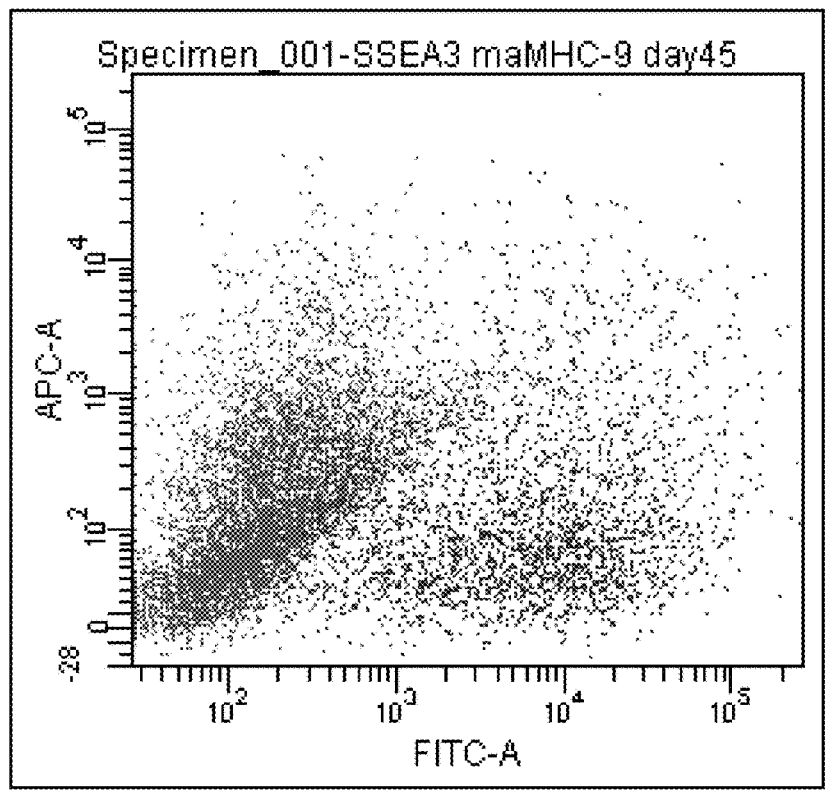
Figure 4I:
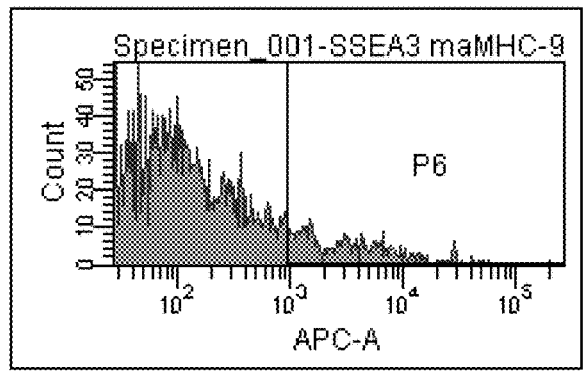
Figure 4I:
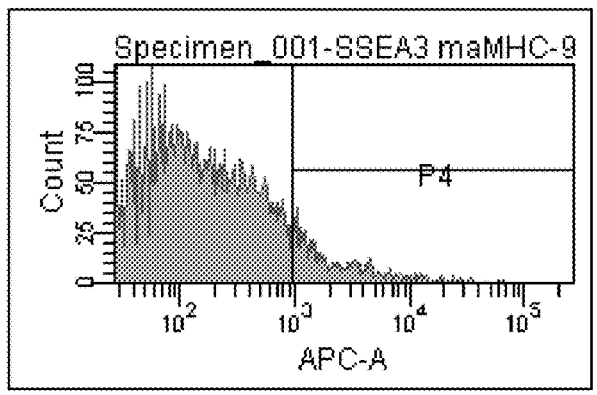
Figure 4J:
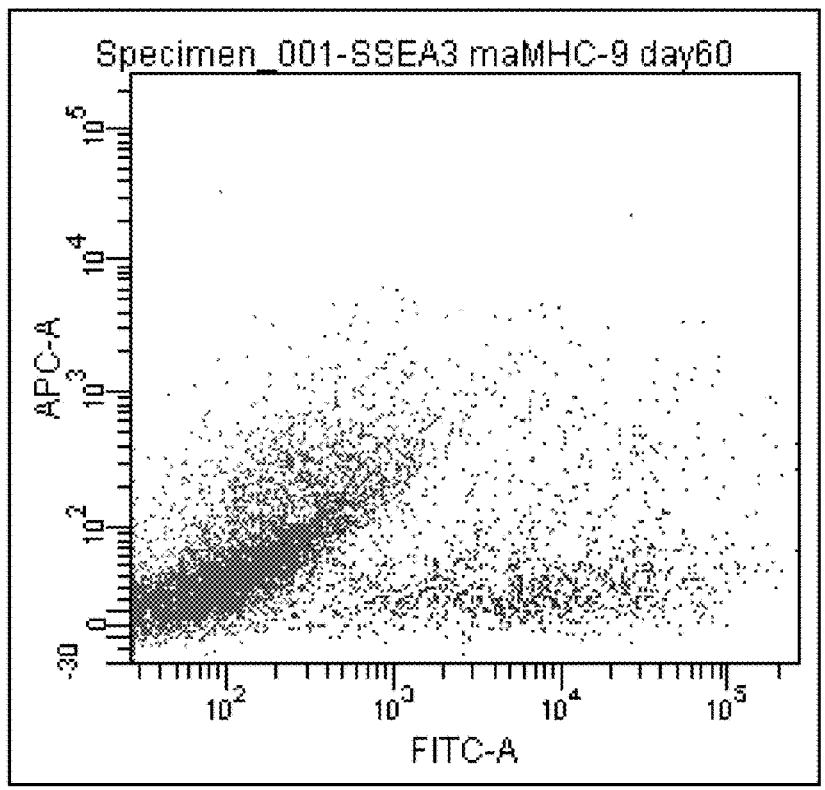
Figure 4J:
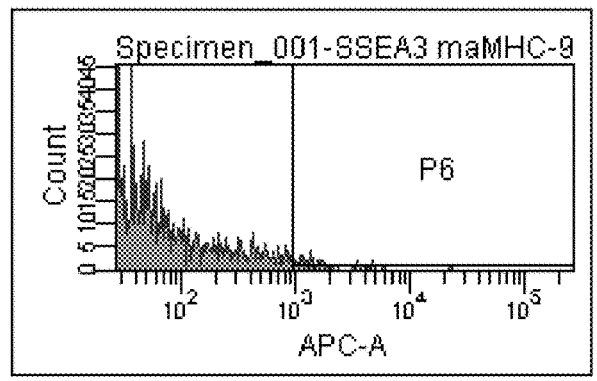
Figure 4J:
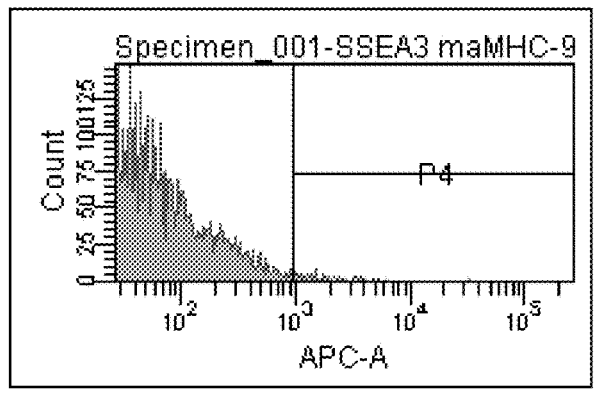
Figure 5A:
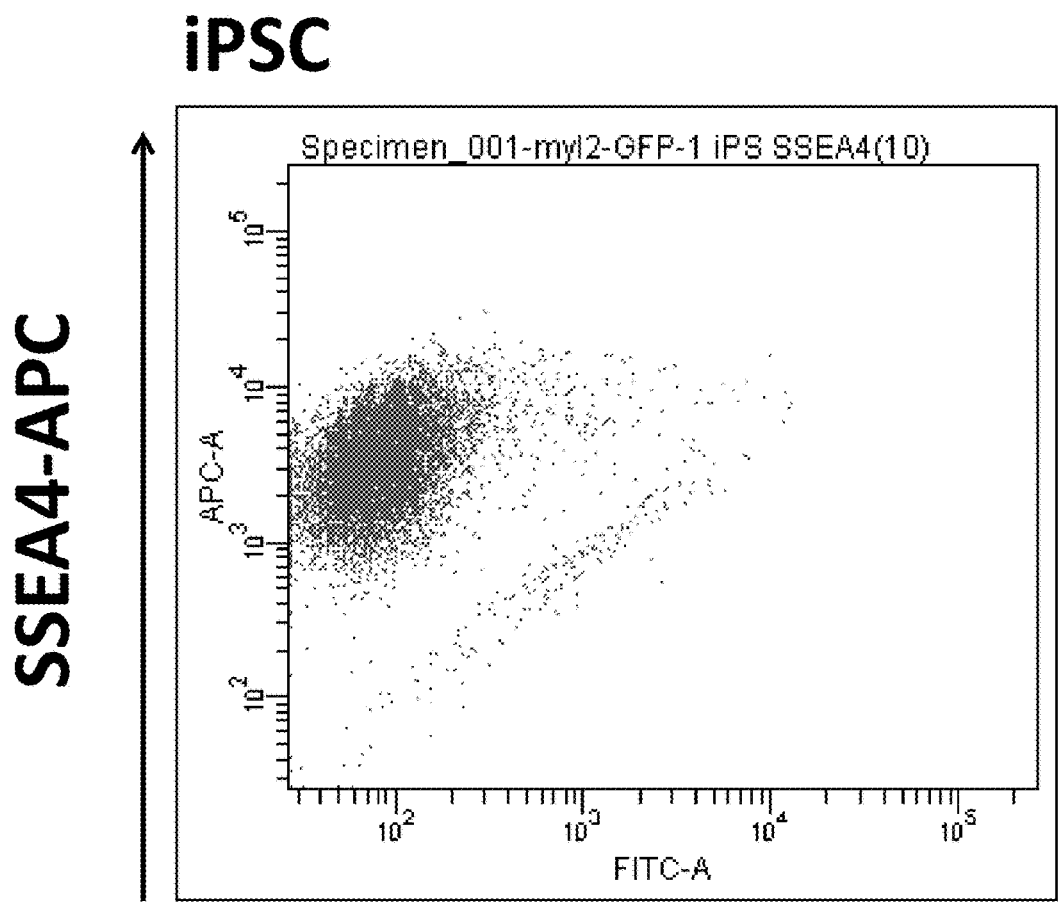
FIGS. 5A-5J illustrate the results of flow cytometry on Day 0 (FIG. 5A), Day 4 (FIG. 5B), Day 8 (FIG. 5C), Day 12 (FIG. 5D), Day 16 (FIG. 5E), Day 20 (FIG. 5F), Day 26 (FIG. G), Day 33 (FIG. 5H), Day 45 (FIG. 5I) and Day 60 (FIG. 5J) after the beginning of induction of differentiation of the 201B7-M6GIP4 strain.
Figure 5B:
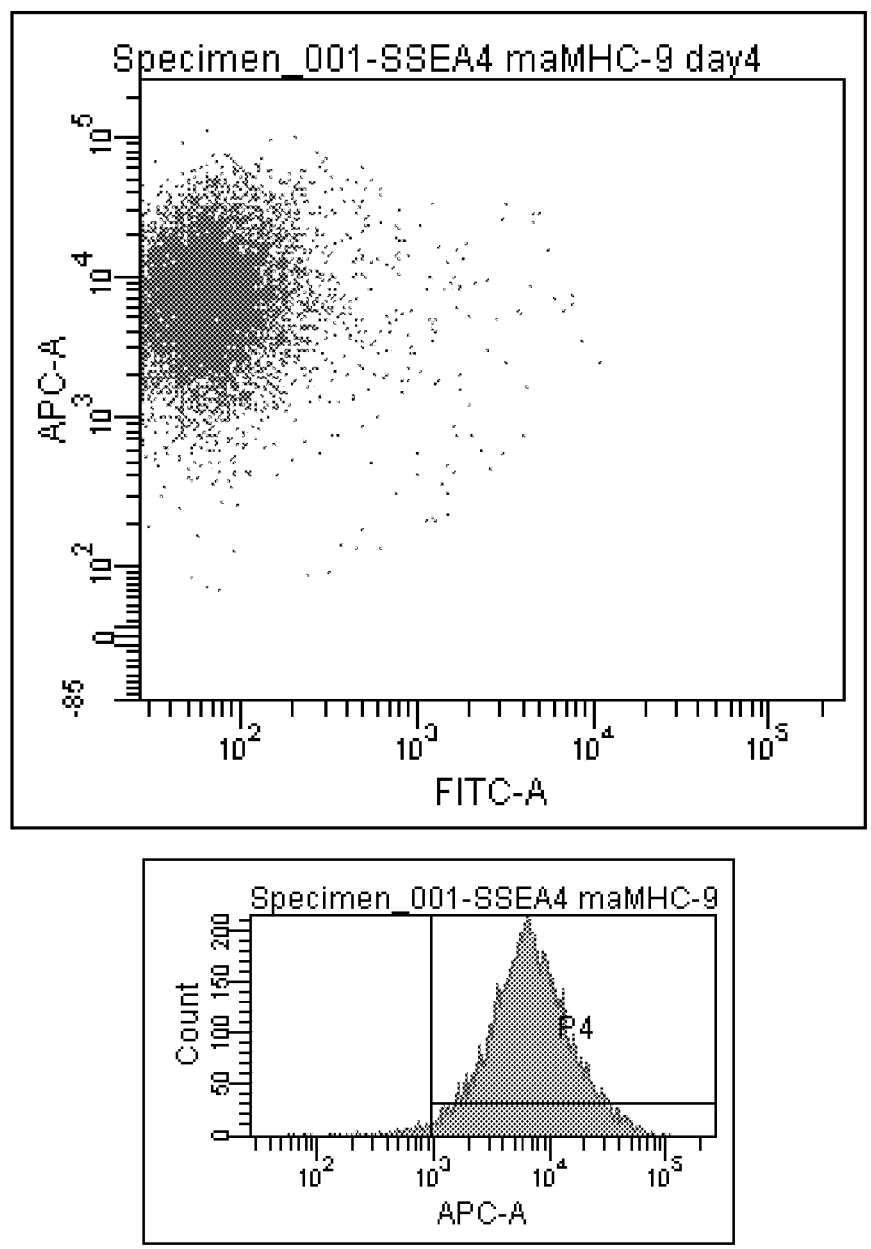
Figure 5C:
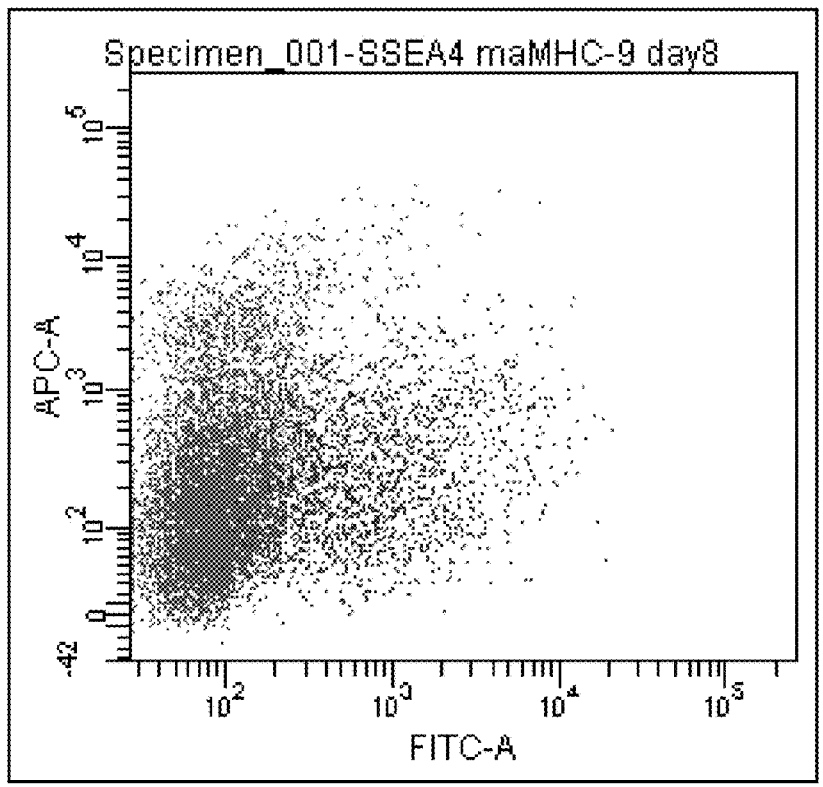
Figure 5C:
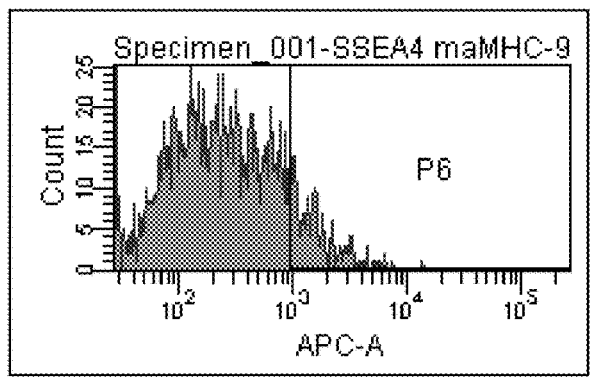
Figure 5C:
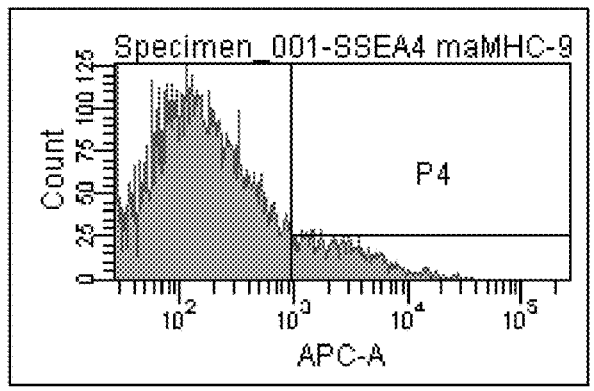
Figure 5D:
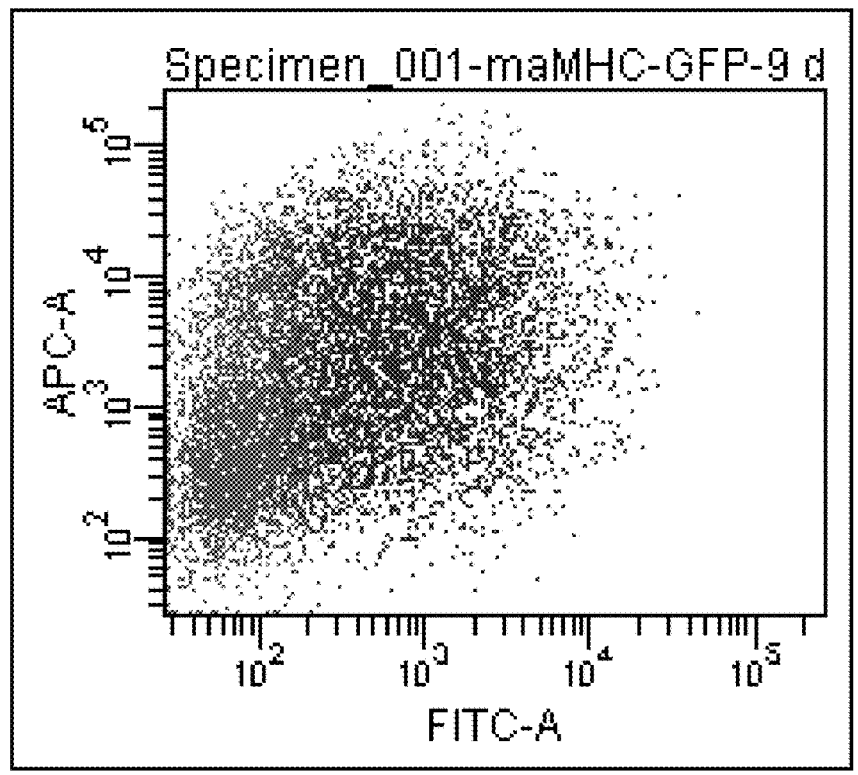
Figure 5D:
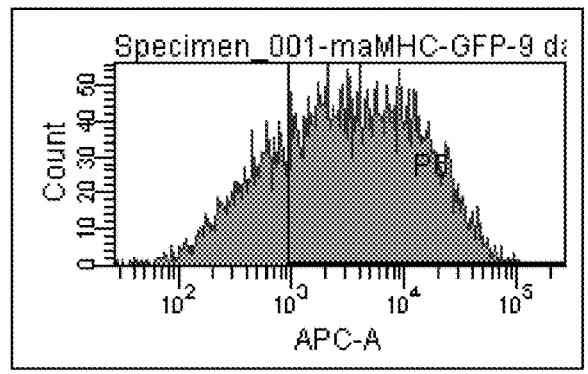
Figure 5D:
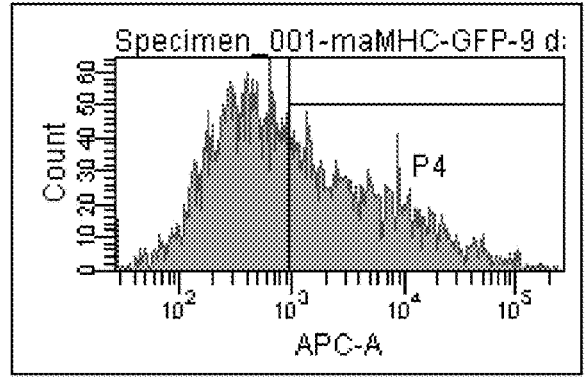
Figure 5E:
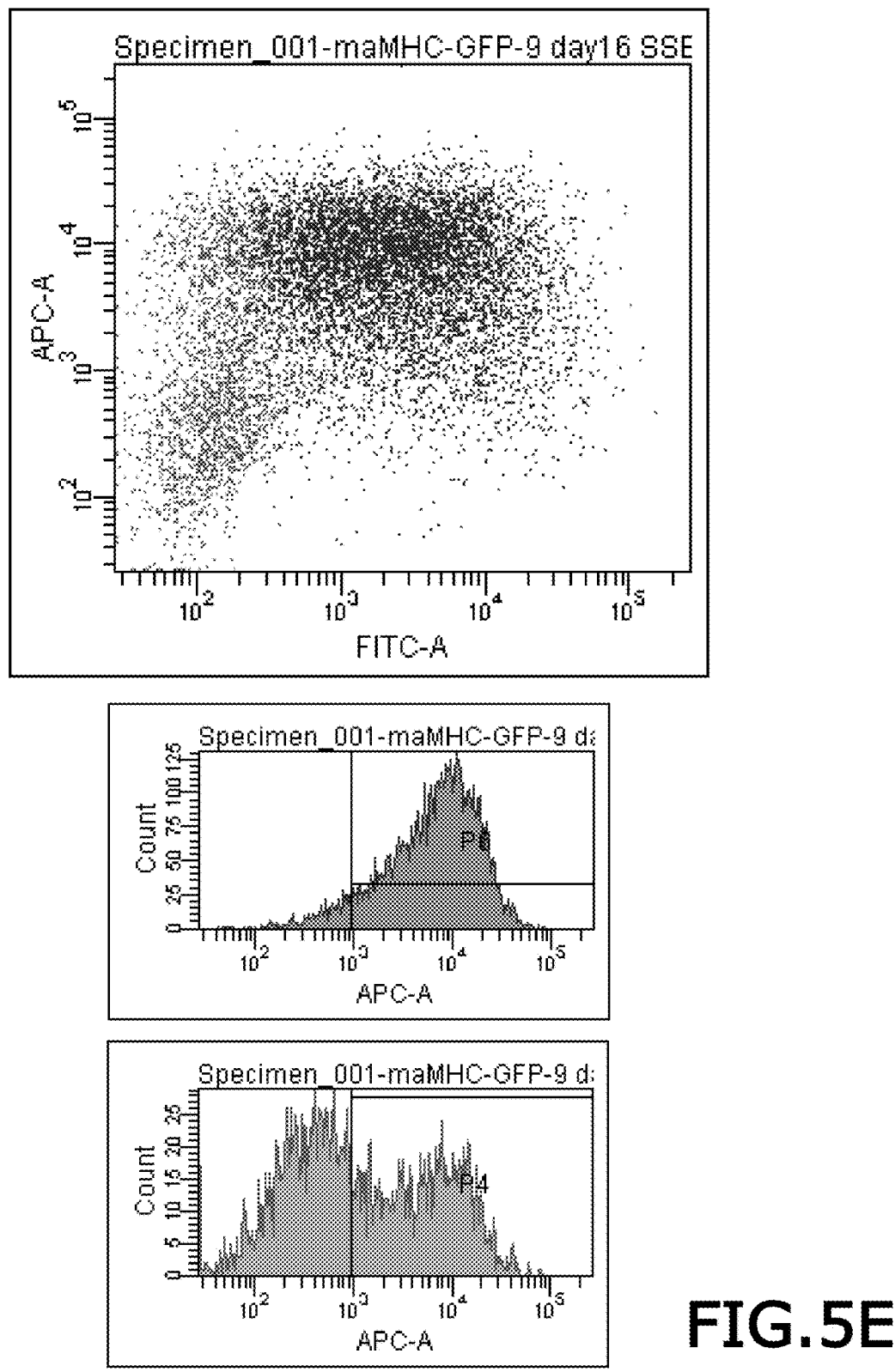
Figure 5F:
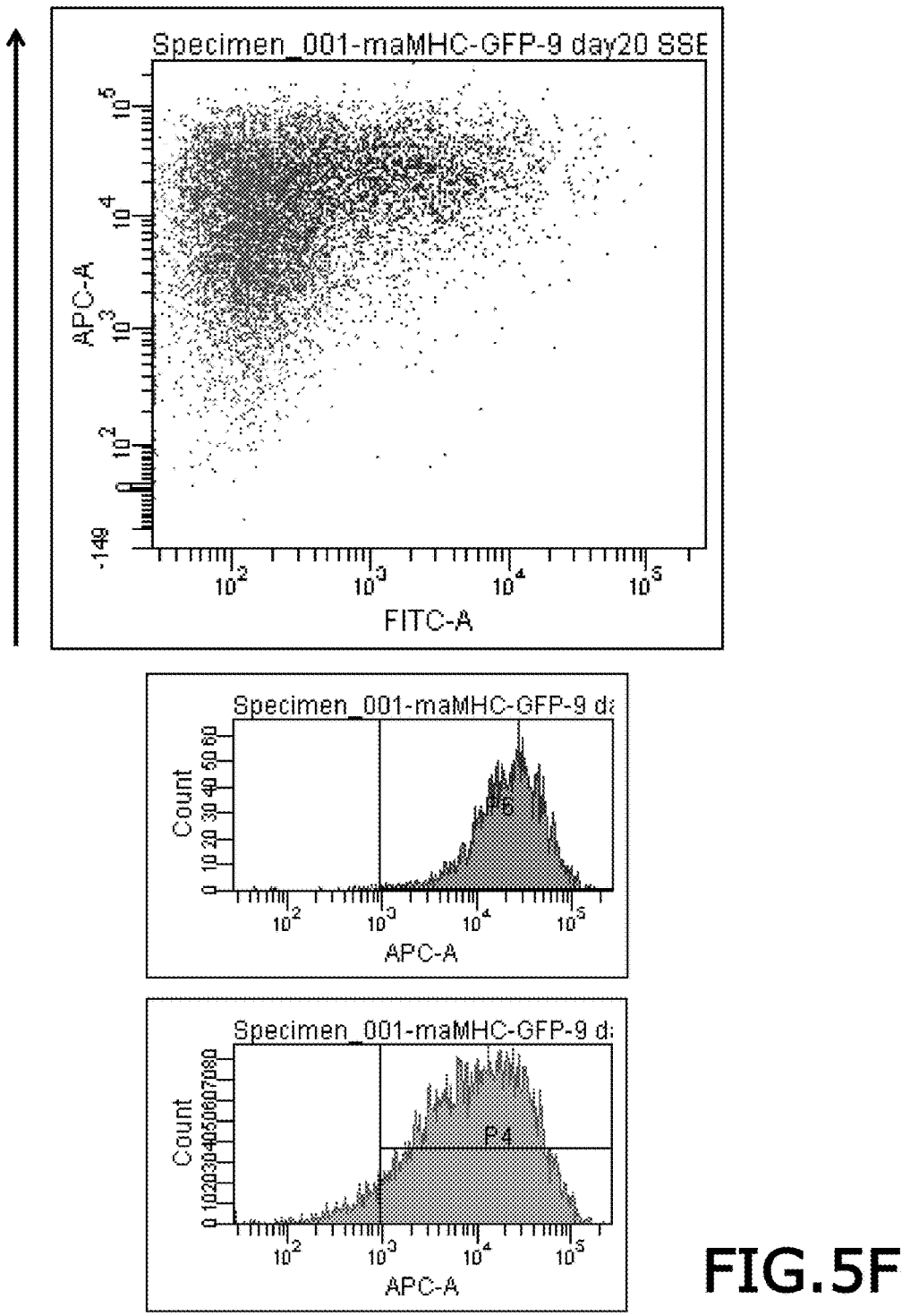
Figure 5G:
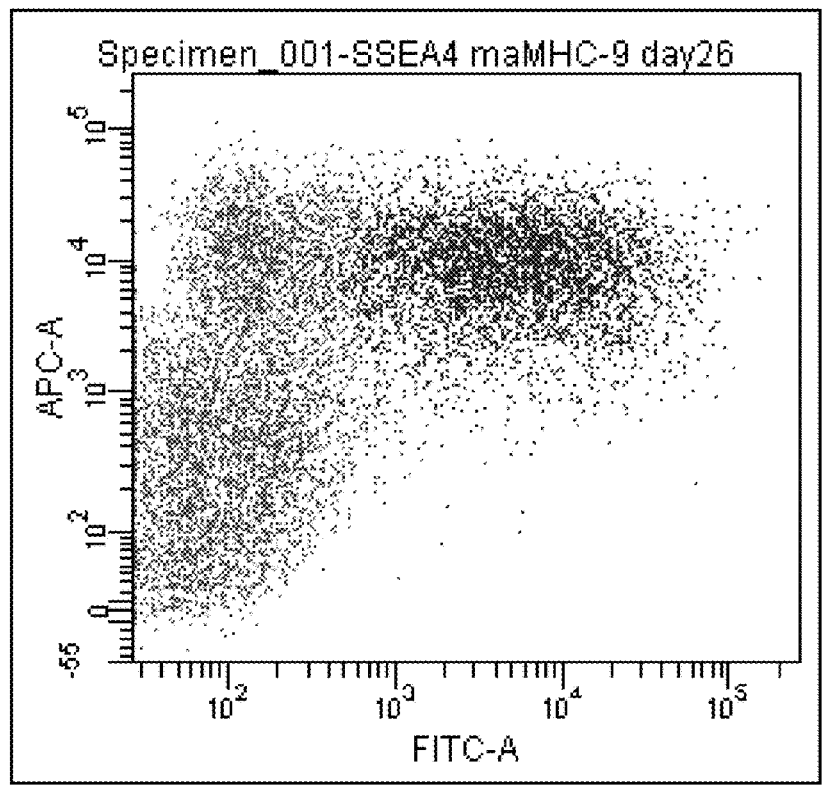
Figure 5G:
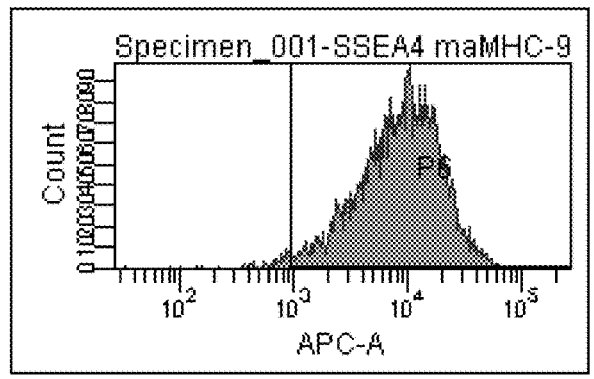
Figure 5G:
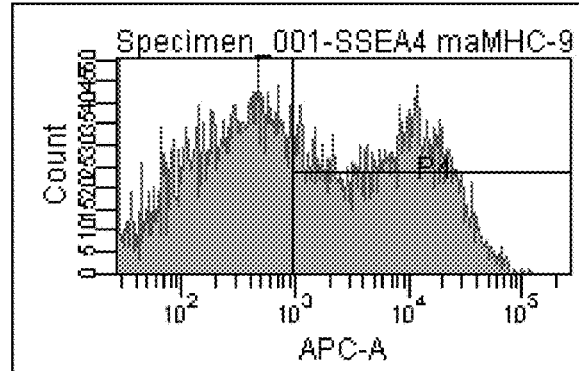
Figure 5H:
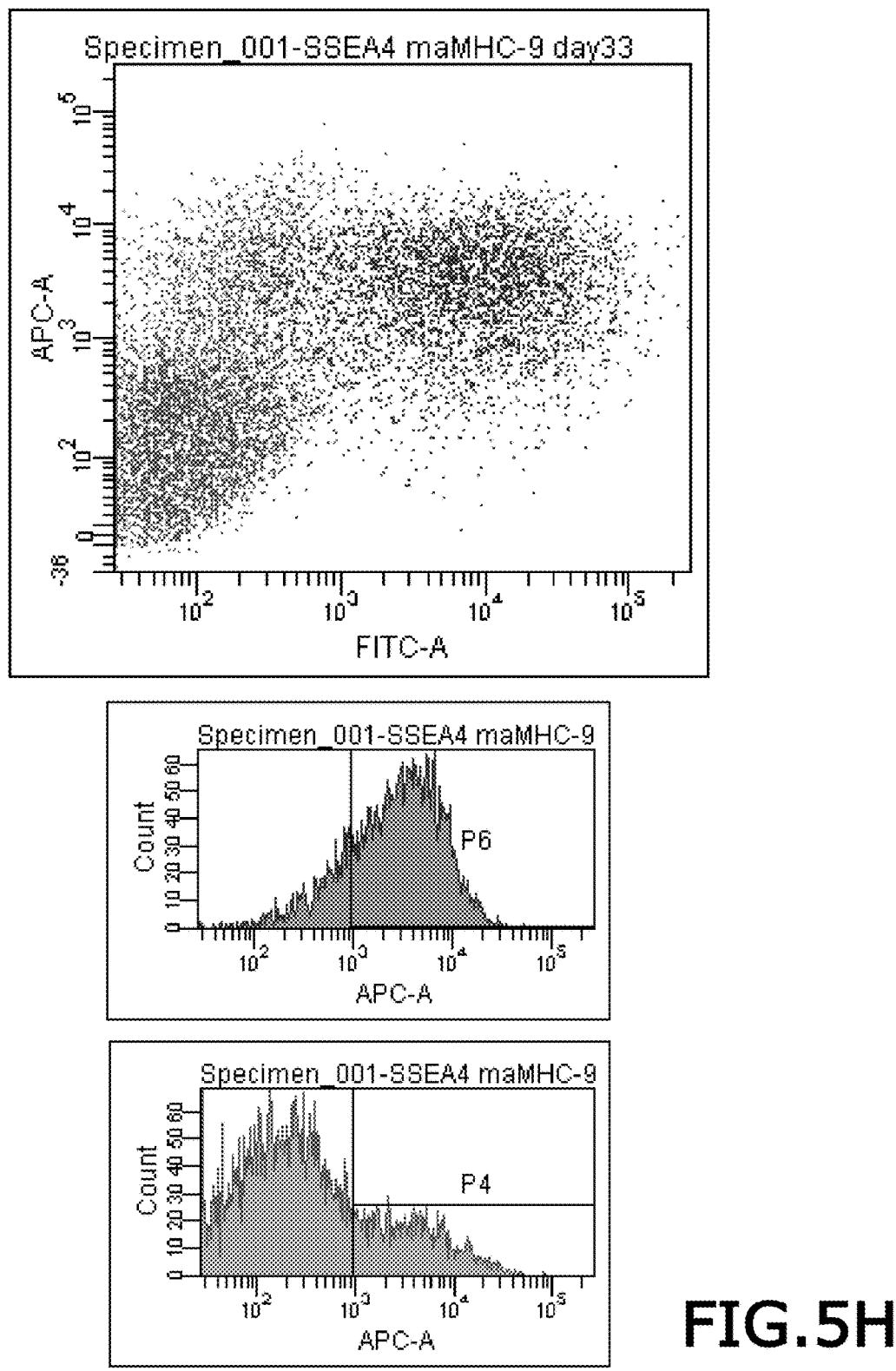
Figure 5I:
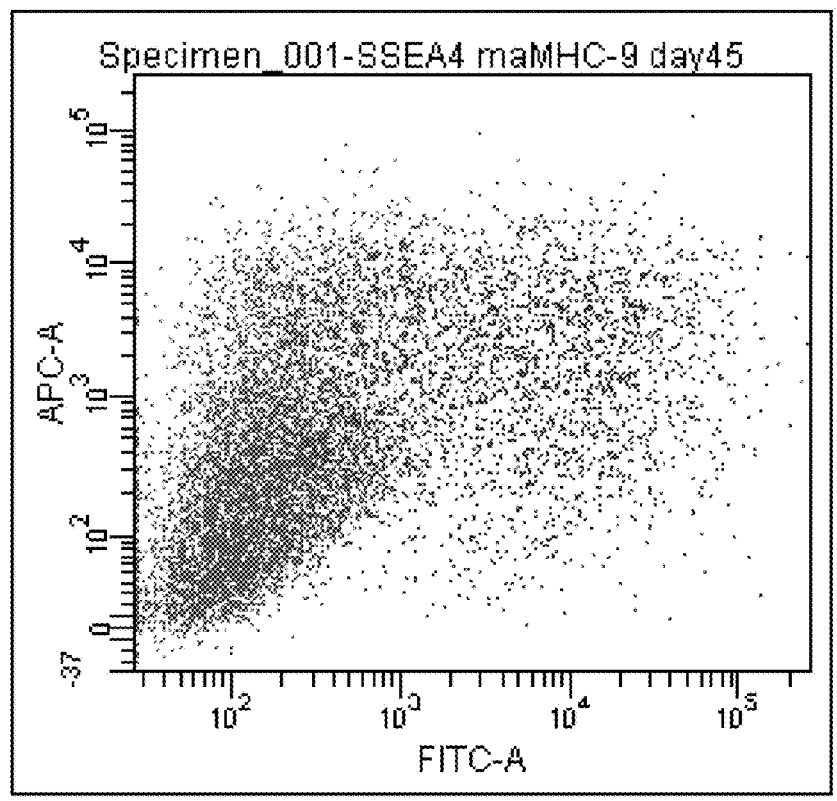
Figure 5I:
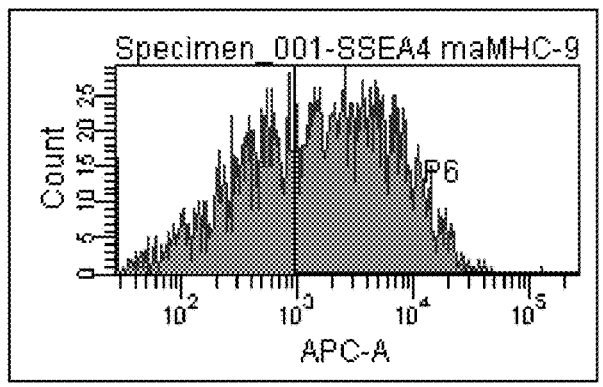
Figure 5I:
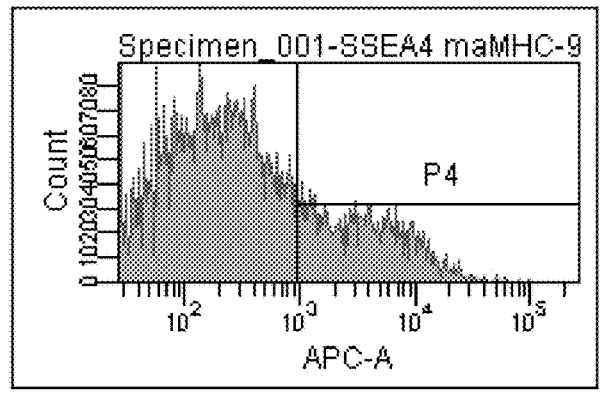
Figure 5J:
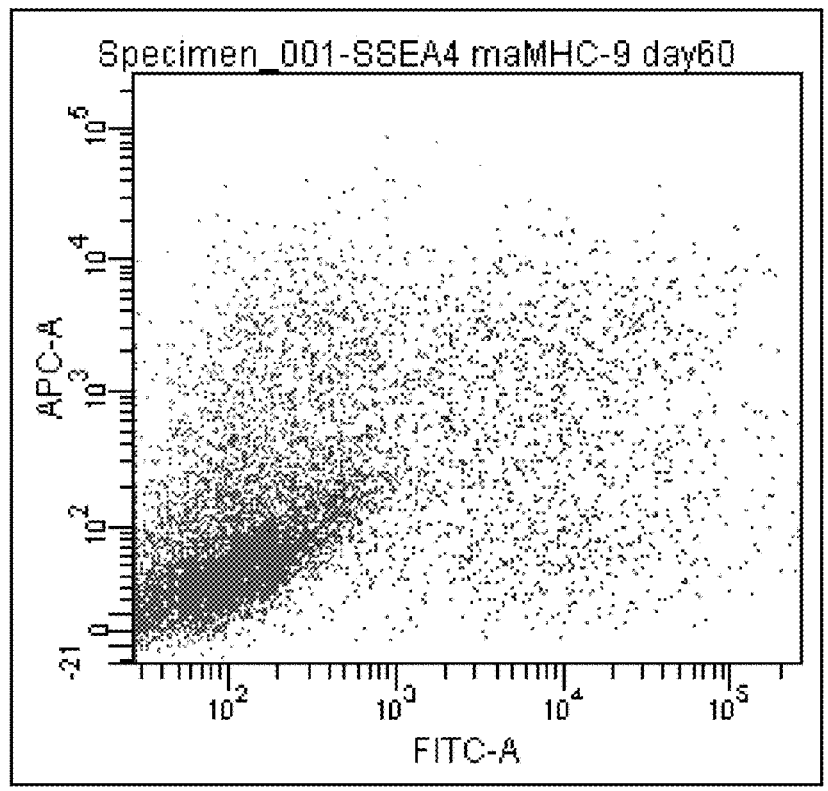
Figure 5J:
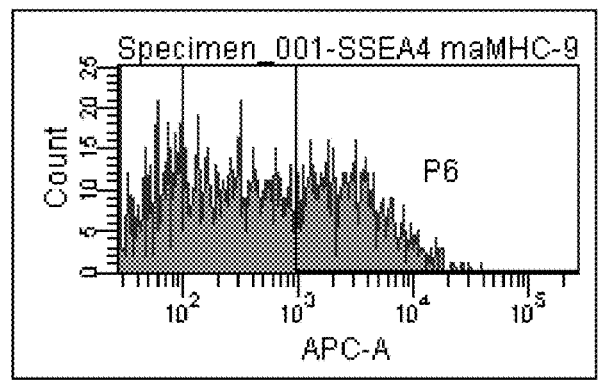
Figure 5J:
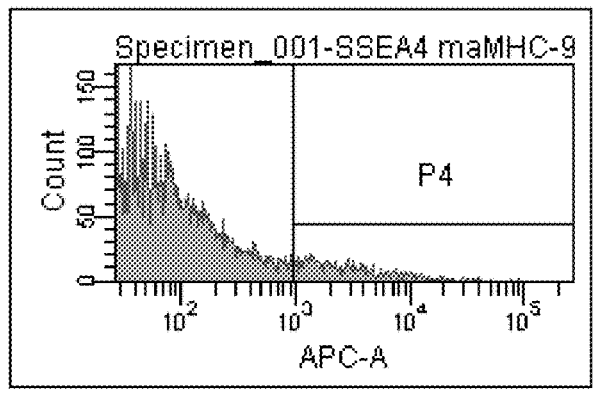
Figure 6A:
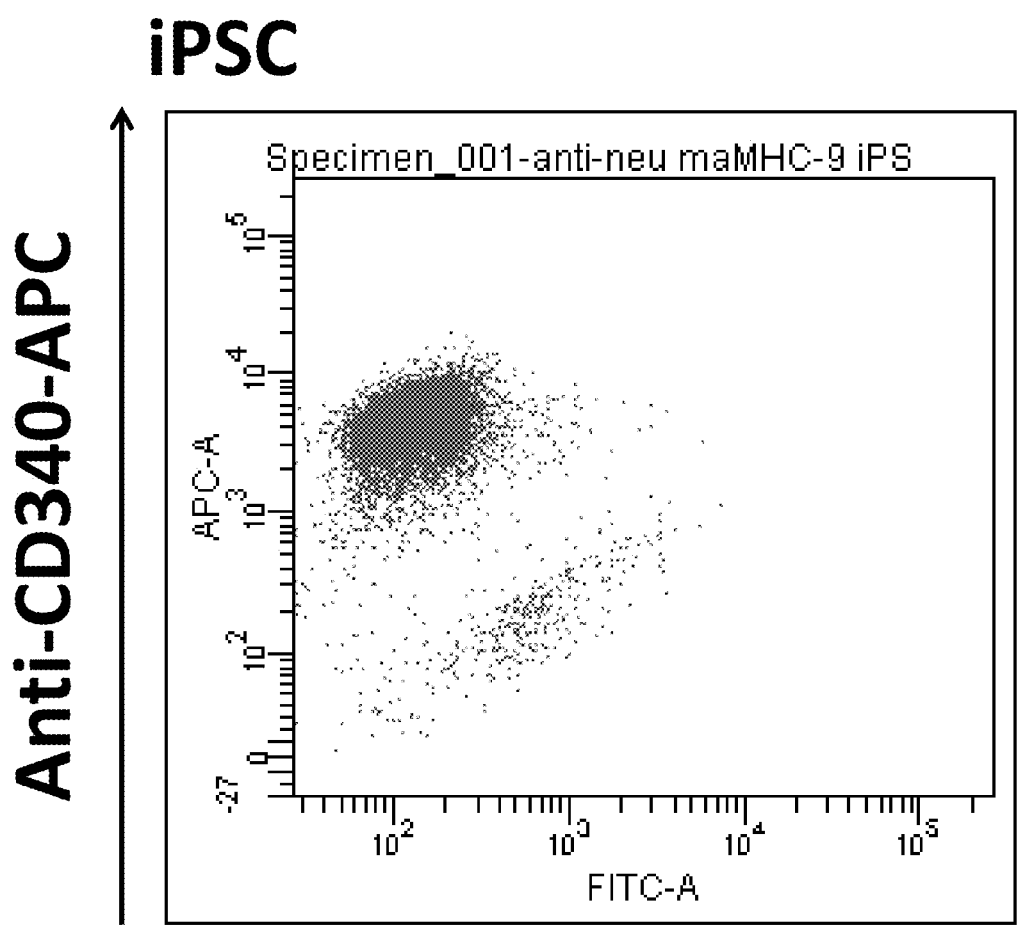
FIGS. 6A-6H illustrate the results of flow cytometry on Day 0 (FIG. 6A), Day 4 (FIG. 6B), Day 8 (FIG. 6C), Day 12 (FIG. 6D), Day 16 (FIG. 6E), Day 20 (FIG. 6F), Day 30 (FIG. 6G), and Day 45 (FIG. 6H) after the beginning of induction of differentiation of the 201B7-M6GIP4 strain.
Figure 6B:
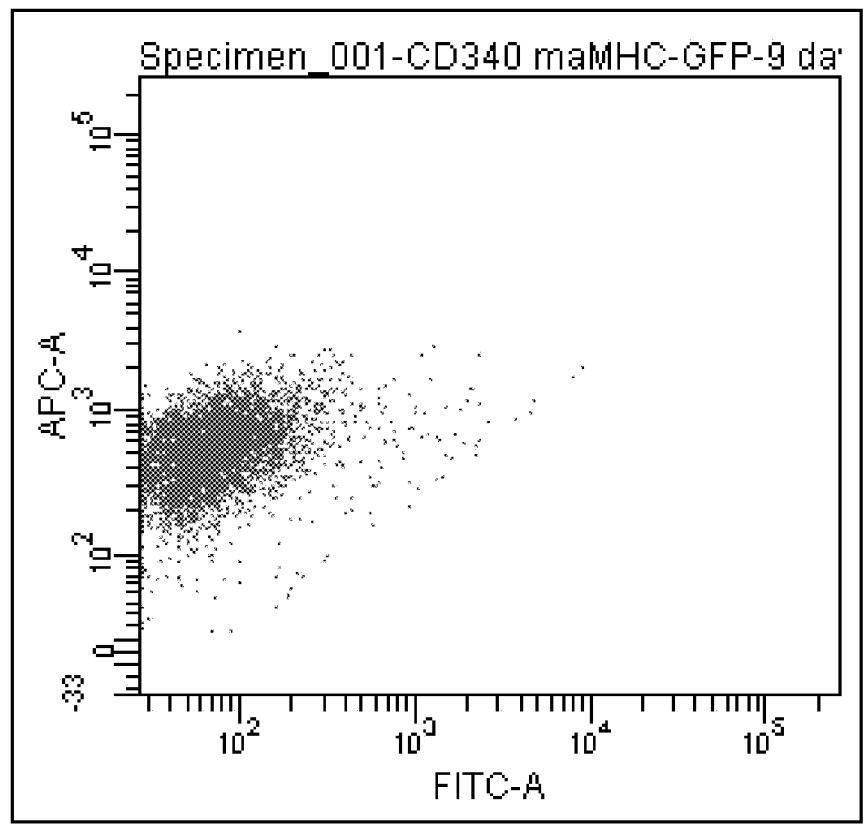
Figure 6B:
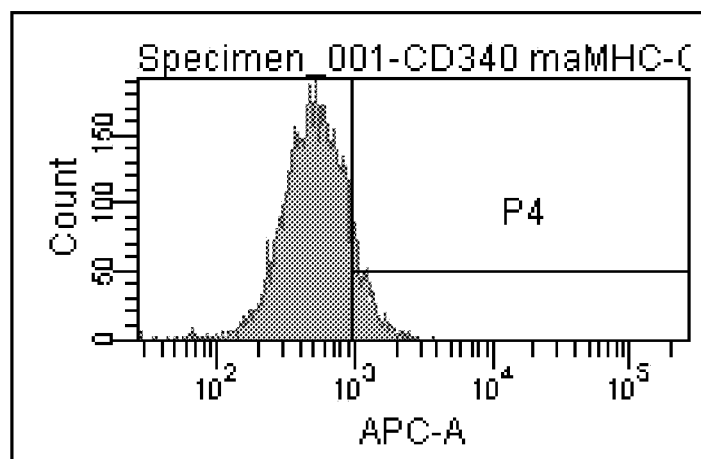
Figure 6C:
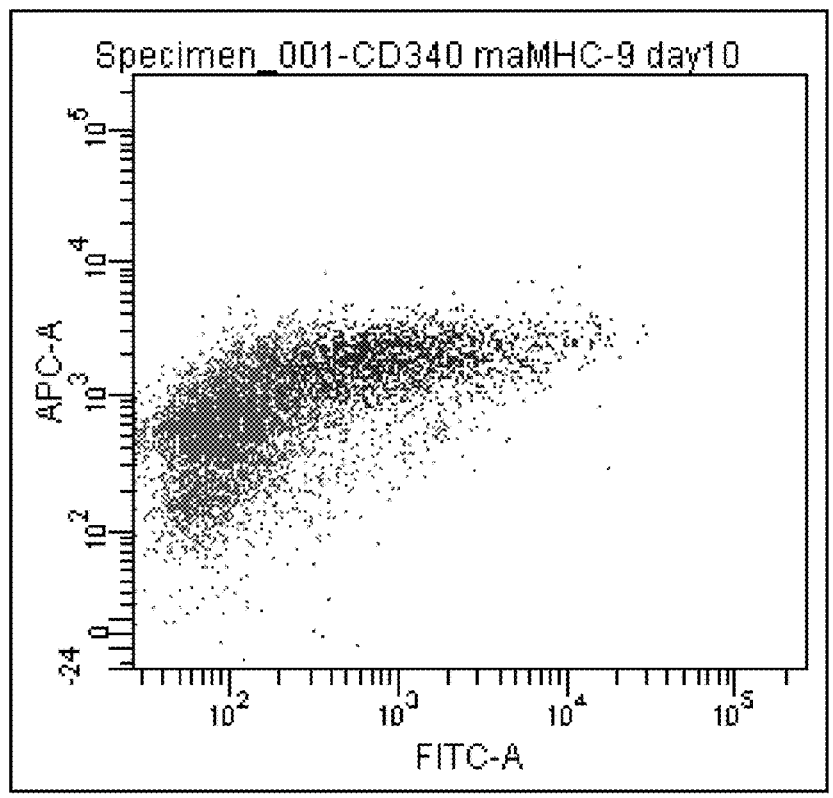
Figure 6C:
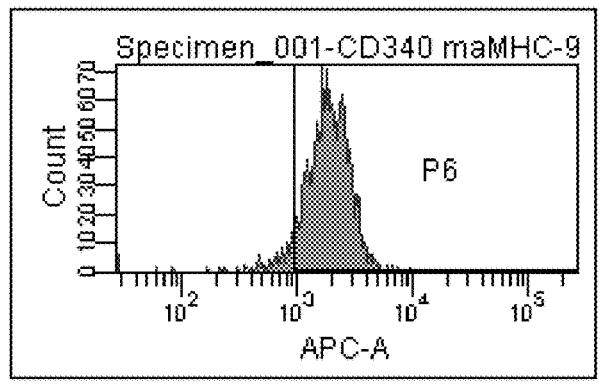
Figure 6C:
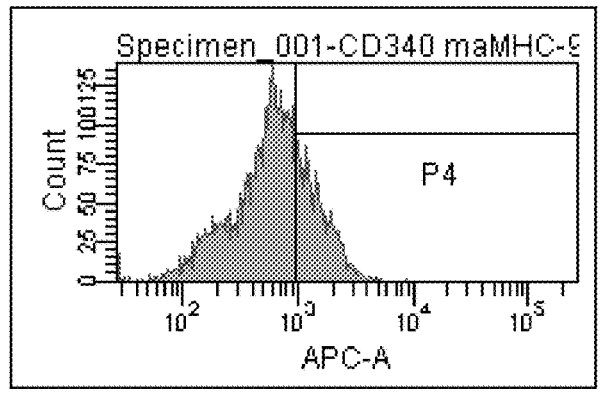
Figure 6D:
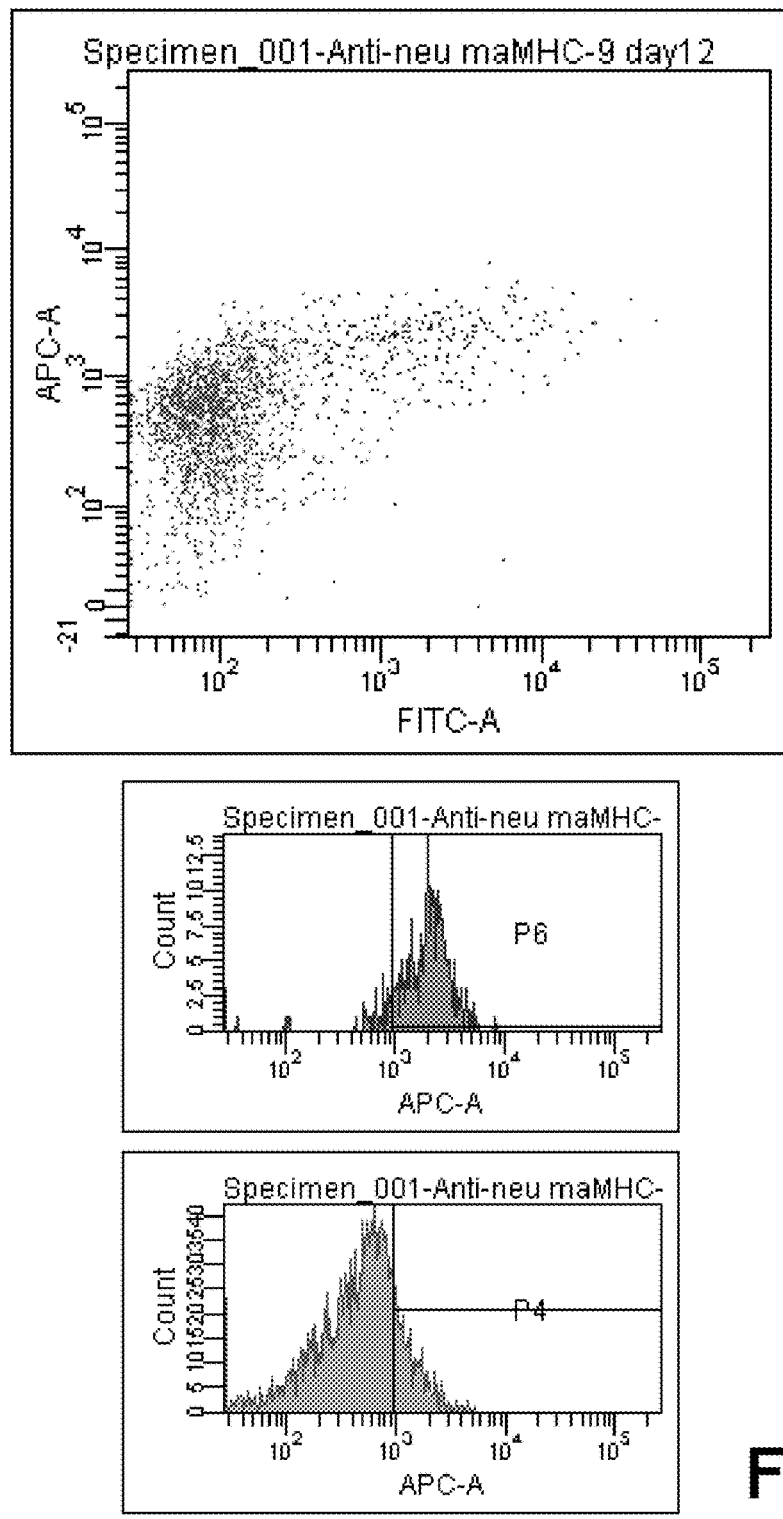
Figure 6E:
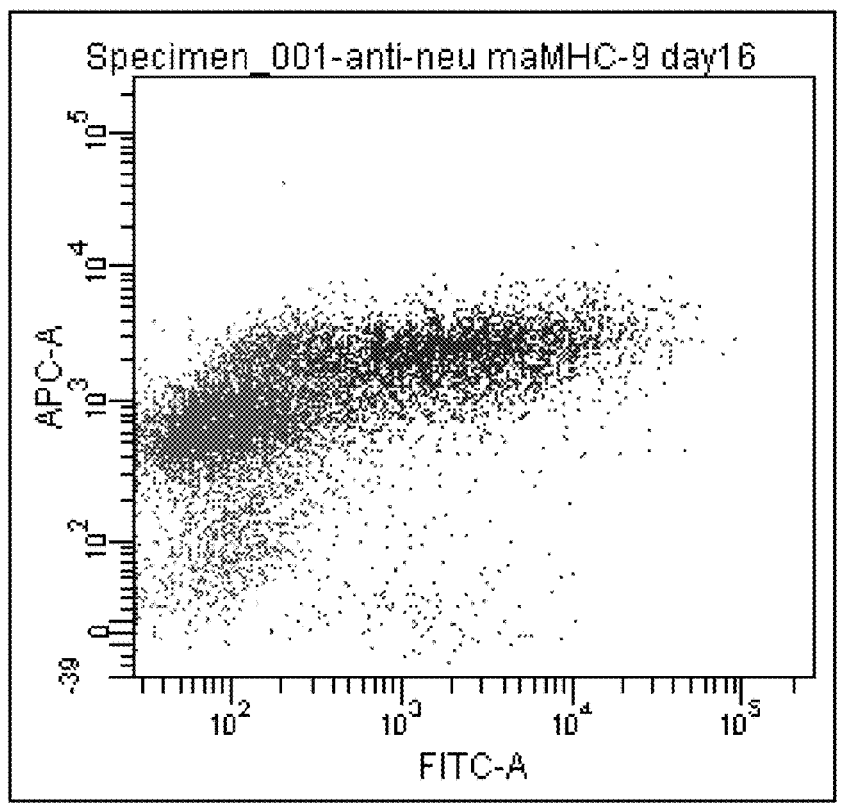
Figure 6E:
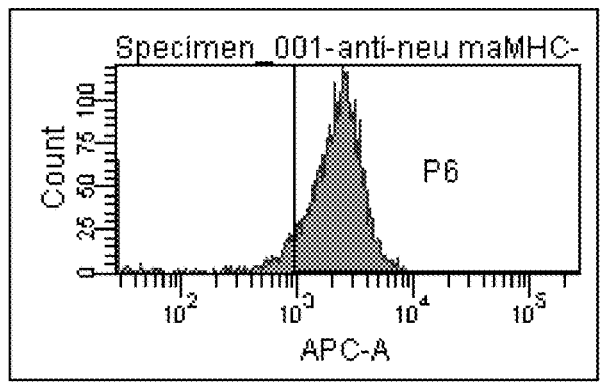
Figure 6E:
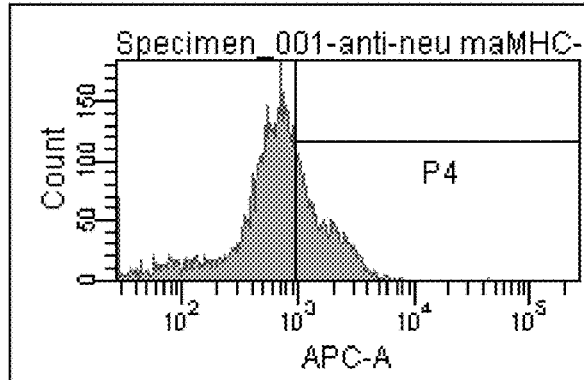
Figure 6F:
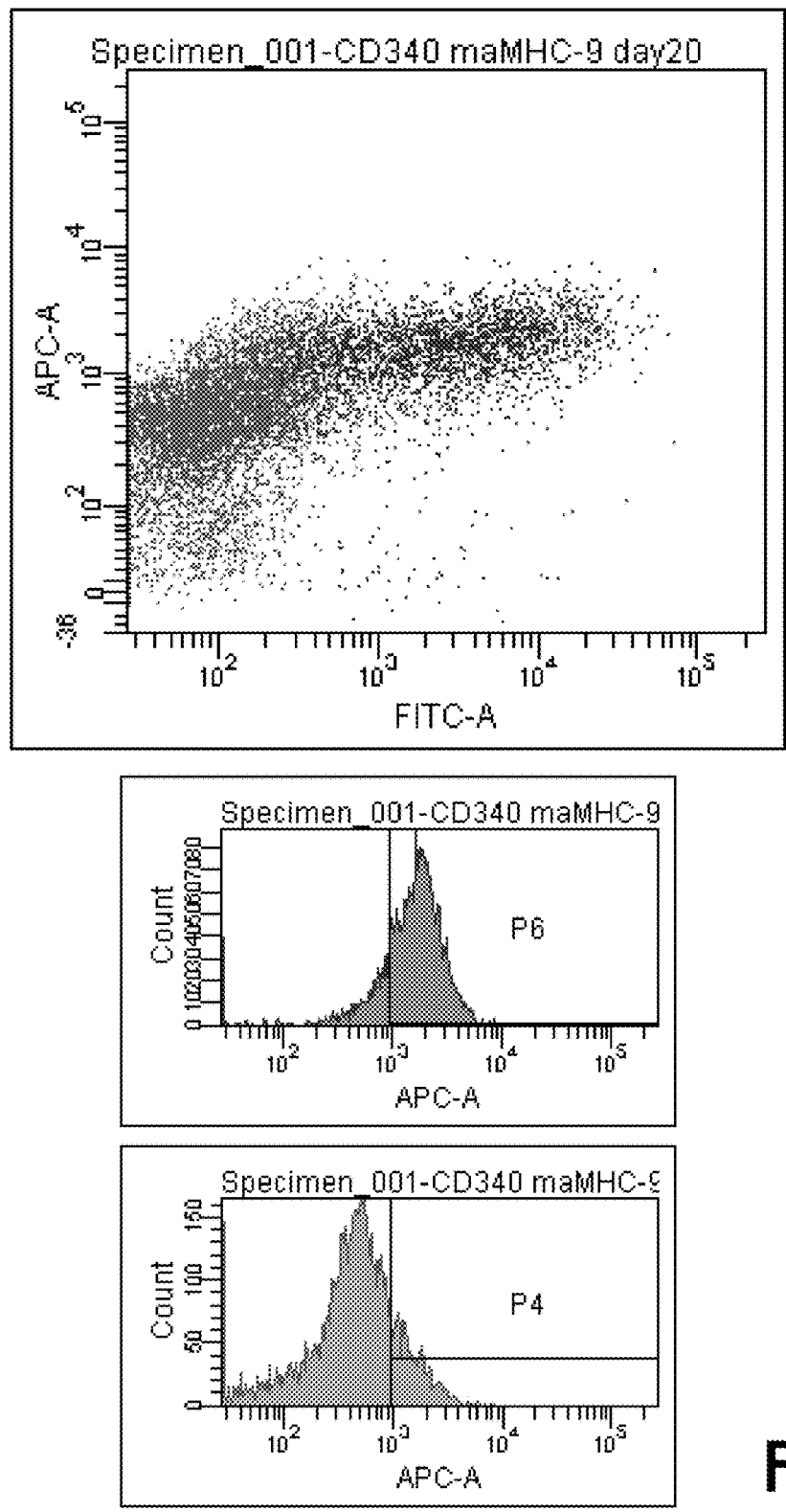
Figure 6G:
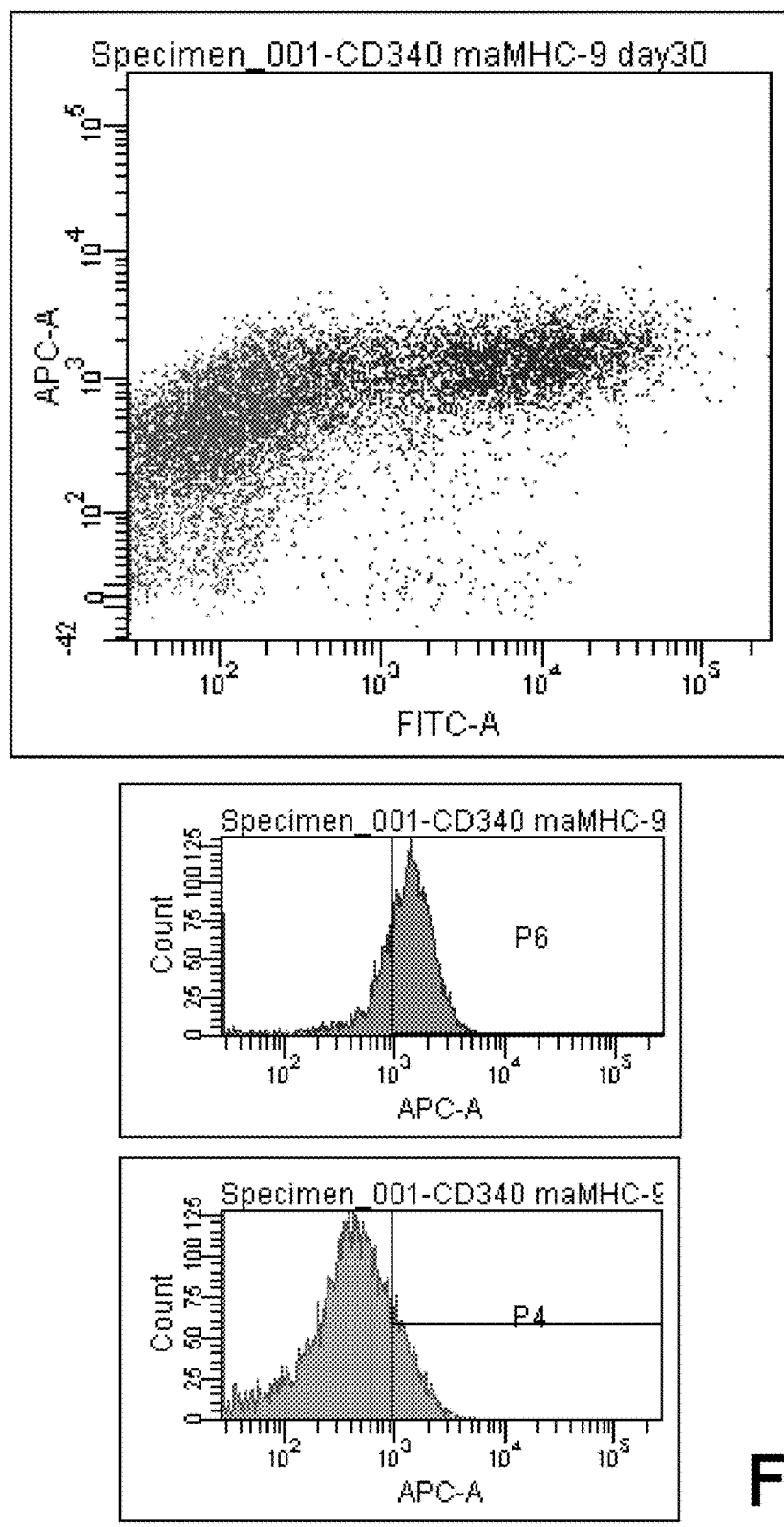
Figure 6H:
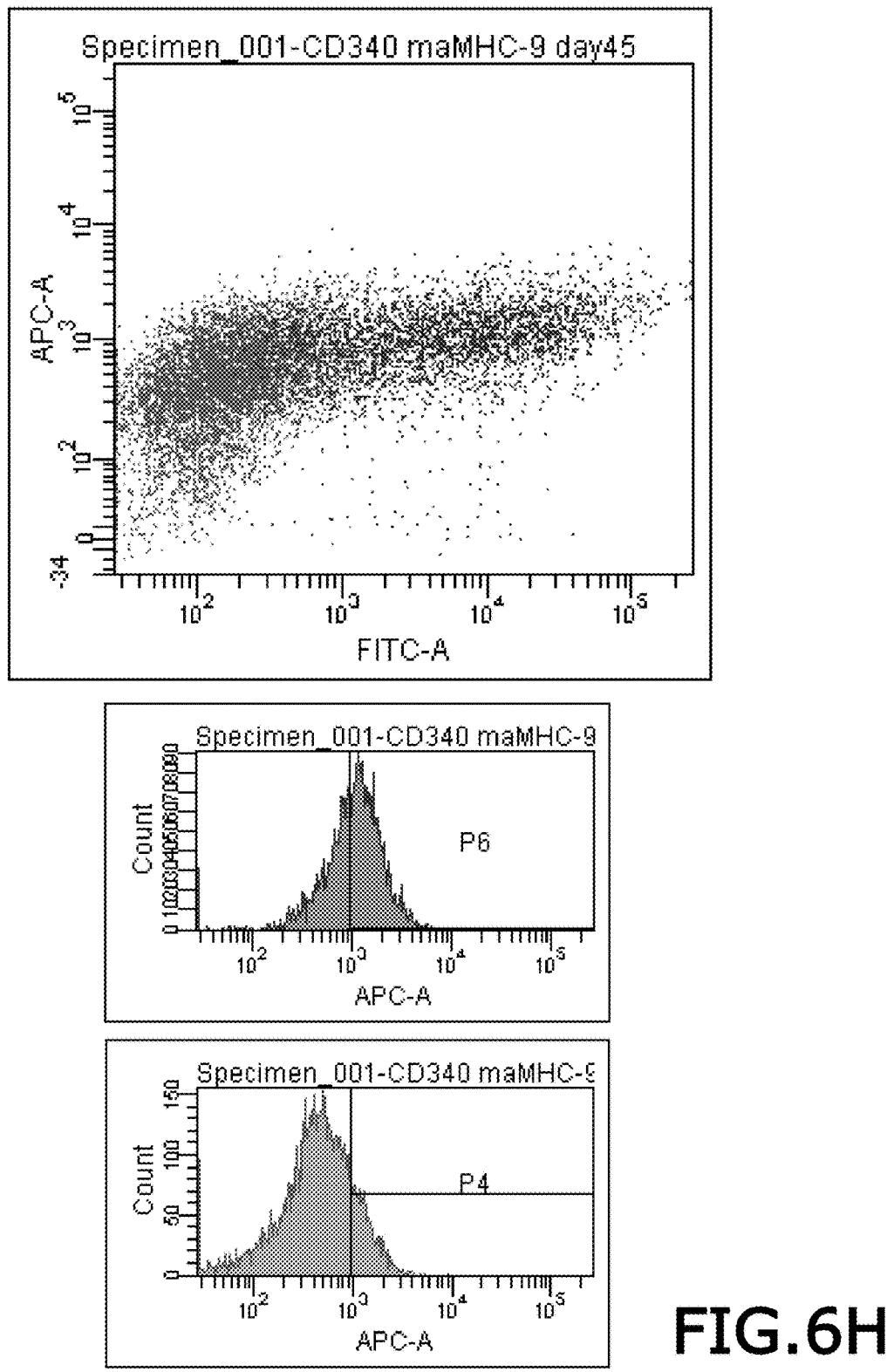

The human iPS cell (201B7-M6GIP4 strain and 606A1 strain)-derived cardiomyocytes induced by the method described in Example 2 were stained with an anti-NCAM1 antibody (BD) on Day 0, Day 4, Day 8, Day 12, Day 16, Day 20, Day 26, Day 33, Day 45 and Day 60 after the induction, and evaluated using flow cytometry (FIG. 2). As a result of cardiomyocyte purification based on the difference in expression of NCAM1 on Day 30, the ratio of troponin T-positive cardiomyocytes, which was 58.5% before the purification, became 88.6% and 71.3% in NCAM1-highly expressing cells and NCAM1-moderately expressing cells, respectively, obtained by sorting by flow cytometry (FIG. 3). Thus, highly pure cardiomyocytes were obtained.

The above results showed that cardiomyocytes can be identified by using NCAM1 as an index of differentiation into cardiomyocytes.

Example 4

Evaluation of Cells with Cardiomyocyte Marker SSEA3

The human iPS cell (201B7-M6GIP4 strain and 606A1 strain)-derived cardiomyocytes induced by the method described in Example 2 were stained with an anti-SSEA3 antibody (BD) on Day 0, Day 4, Day 8, Day 12, Day 16, Day 20, Day 26, Day 33, Day 45 and Day 60 after the induction, and evaluated using flow cytometry. As a result, immature cardiomyocytes on Day 8 were negative for the marker, but high expression was observed in a part of MYH6-positive cardiomyocytes on Day 16 to Day 26 (FIG. 4).

As a result of cardiac muscle purification based on the difference in expression of SSEA3 on Day 16, the ratio of MYH6-positive cells, which was 69.7% before the purification, became as high as 81.5% after the purification.

The above results showed that cardiomyocytes can be identified by using SSEA3 as an index of differentiation into cardiomyocytes.

Example 5

Evaluation of Cells with Cardiomyocyte Marker SSEA4

The human iPS cell (201B7-M6GIP4 strain and 606A1 strain)-derived cardiomyocytes induced by the method described in Example 2 were stained with an anti-SSEA4 antibody (BD) on Day 0, Day 4, Day 8, Day 12, Day 16, Day 20, Day 26, Day 33, Day 45 and Day 60 after the induction, and evaluated using flow cytometry. As a result, immature cardiomyocytes on Day 8 were negative for the marker, but high expression was observed in many of MYH6-positive cardiomyocytes on Day 12 and later, and high expression was observed in most of MYH6-positive cardiomyocytes especially on Day 12 to Day 33 (FIG. 5).

As a result of cardiac muscle purification based on the difference in expression of SSEA4 on Day 16, the ratio of MYH6-positive cells, which was 69.7% before the purification, became as high as 84.0% after the purification.

The above results showed that cardiomyocytes can be identified by using SSEA4 as an index of differentiation into cardiomyocytes.

Example 6

Evaluation of Cells with Cardiomyocyte Marker CD340

The human iPS cell (201B7-M6GIP4 strain and 606A1 strain)-derived cardiomyocytes induced by the method described in Example 2 were stained with an anti-CD340 antibody (BD) on Day 0, Day 4, Day 8, Day 12, Day 16, Day 20, Day 30 and Day 45 after the induction, and evaluated using flow cytometry. As a result, MYH6-positive cardiomyocytes were CD340-positive on Day 8 and later after the induction (FIG. 6). As a result of cardiac muscle purification based on the difference in expression of CD340 on Day 16 and Day 30, the ratio of MYH6-positive cells on Day 16, which was 35.7% before the purification, became 71.2% after the purification, and the ratio on Day 30, which was 36.7% before the purification, became 65.7% after the purification.

The above results showed that cardiomyocytes can be identified by using CD340 as an index of differentiation into cardiomyocytes.

INDUSTRIAL APPLICABILITY

According to the present invention, cardiomyocytes can be efficiently extracted or detected from a cell population comprising the cardiomyocytes.

While the present invention has been described with emphasis on preferred embodiments, it is obvious to those skilled in the art that the preferred embodiments can be modified. The present invention intends that the present invention can be embodied by methods other than those described in detail in the present specification. Accordingly, the present invention encompasses all modifications encompassed in the gist and scope of the appended "CLAIMS."

The contents disclosed in any publication cited herein, including patents and patent applications, are hereby incorporated in their entireties by reference, to the extent that they have been disclosed herein.

What is claimed is:

1. A method for concentrating a cardiomyocyte(s), which are positive for cardiac troponin and/or α myosin heavy chain, comprising
    a) providing a pluripotent stem cell-derived cell population comprising the cardiomyocytes, that is obtained by inducing differentiation of the pluripotent stem cells under conditions that promote differentiation into cardiomyocytes, and
    b) extracting from the cell population cells which are positive for the at least one marker selected from the group consisting of SSEA3 (Stage-Specific Embryonic Antigen-3) and SSEA4 (Stage-Specific Embryonic Antigen-4) so as to concentrate the cardiomyocyte(s) which is/are positive for cardiac troponin and/or a myosin heavy chain.

2. The method according to claim 1, wherein said cardiomyocyte is human cardiomyocyte.

3. The method according to claim 1, wherein said cell population comprising cardiomyocyte(s) is
    a cell population obtained by inducing differentiation of a pluripotent stem cell(s) into cardiomyocytes.

4. The method according to claim 3, wherein said pluripotent stem cell is an ES (embryonic stem) cell or iPS (induced pluripotent stem) cell.

5. The method according to claim 3, wherein said induction of differentiation into a cardiomyocyte(s) comprises forming an embryoid body.

6. The method according to claim 4, wherein said induction of differentiation into a cardiomyocyte(s) comprises culturing an embryoid body in a medium comprising a cytokine(s).

7. The method according to claim 6, wherein said cytokine(s) is at least one cytokine selected from the group consisting of activin A, BMP4 (Bone Morphogenetic Protein 4), b-FGF (basic fibroblast growth factor), and VEGF (vascular endothelial growth factor).

8. The method according to claim 6, wherein said medium further comprises a Wnt inhibitor.

9. The method according to claim 8, wherein said Wnt inhibitor is DKK-1 (Dickkopf-related protein 1).

10. The method according to claim 1, wherein cells expressing said at least one marker are extracted from the cell population by contacting the cell population with one or more reagents having specific affinity to said at least one marker.

11. The method according to claim 1, wherein the cardiomyocyte(s) is/are also positive for CD340, and wherein step b) comprises extracting from the cell population, after induction, cells which are positive for the at least one marker selected from the group consisting of SSEA3 and SSEA4, and are also positive for CD340.

12. A method for detecting a cardiomyocyte(s) which are positive for cardiac troponin and/or α myosin heavy chain, comprising detecting in a cell population comprising cardiomyocytes obtained by inducing differentiation of pluripotent stem cells under conditions that promote differentiation into cardiomyocytes, cells which are positive for at least one marker selected from the group consisting of SSEA3 and SSEA4.

13. The method according to claim 12, wherein said cardiomyocyte is a human cardiomyocyte.

14. The method according to claim 12, wherein said cell population comprising a cardiomyocyte is
a cell population obtained by inducing differentiation of a pluripotent stem cell(s).

15. The method according to claim 12, wherein said pluripotent stem cell is an ES cell or iPS cell.

16. The method according to claim 12, wherein cells expressing said at least one marker are detected in the cell population by contacting the cell population with one or more reagents having specific affinity to said at least one marker.

17. The method according to claim 10, wherein the cardiomyocyte(s) is/are also positive for CD340, and wherein the cells detected are positive for at least one marker selected from the group consisting of SSEA3 and SSEA4, and are also positive for CD340.

* * * * *

UNITED STATES PATENT AND TRADEMARK OFFICE
CERTIFICATE OF CORRECTION

PATENT NO. : 10,150,949 B2
APPLICATION NO. : 15/619842
DATED : December 11, 2018
INVENTOR(S) : Shinya Yamanaka Page 1 of 1

It is certified that error appears in the above-identified patent and that said Letters Patent is hereby corrected as shown below:

In the Specification

In Column 6, Line 57, change "ALKS" to --ALK5--.

In Column 9, Line 28, after "be" insert --used.--.

Signed and Sealed this
Sixth Day of August, 2019

Andrei Iancu
*Director of the United States Patent and Trademark Office*